US009368931B2

(12) United States Patent
Bragagna et al.

(10) Patent No.: US 9,368,931 B2
(45) Date of Patent: Jun. 14, 2016

(54) MONOLITHIC, SIDE PUMPED SOLID-STATE LASER AND APPLICATIONS THEREOF

(75) Inventors: Thomas Bragagna, Mauren (LI); Arne Heinrich, Feldkirch (AT)

(73) Assignee: Pantec Biosolutions AG, Ruggell (LI)

( * ) Notice: Subject to any disclaimer, the term of this patent is extended or adjusted under 35 U.S.C. 154(b) by 1188 days.

(21) Appl. No.: 13/378,172

(22) PCT Filed: Jun. 15, 2010

(86) PCT No.: PCT/EP2010/003586
§ 371 (c)(1),
(2), (4) Date: Mar. 5, 2012

(87) PCT Pub. No.: WO2010/145802
PCT Pub. Date: Dec. 23, 2010

(65) Prior Publication Data
US 2012/0165801 A1    Jun. 28, 2012

Related U.S. Application Data

(60) Provisional application No. 61/397,656, filed on Jun. 15, 2010.

(30) Foreign Application Priority Data

Jun. 15, 2009   (WO) ................. PCT/EP2009/057398
Jan. 15, 2010   (WO) ................. PCT/EP2010/050458
Feb. 13, 2010   (WO) ................. PCT/EP2010/051825

(51) Int. Cl.
*H01S 3/14*     (2006.01)
*H01S 3/16*     (2006.01)
(Continued)

(52) U.S. Cl.
CPC ............... *H01S 3/0941* (2013.01); *A61B 18/20* (2013.01); *H01S 3/042* (2013.01); *H01S 3/061* (2013.01);
(Continued)

(58) Field of Classification Search
CPC ....... H01S 3/025; H01S 3/034; H01S 3/0346; H01S 3/04; H01S 3/042; H01S 3/16; H01S 3/1685; H01S 3/17; H01S 5/026; H01S 5/04; H01S 5/0428; A61B 18/20; A61B 18/201; A61B 2018/2015; A61B 2018/202

USPC ......... 372/10, 39, 43.01, 50.1, 69, 70–72, 75; 606/3–14, 16–19; 607/88–92; 250/493.1
See application file for complete search history.

(56) References Cited

U.S. PATENT DOCUMENTS

| 4,808,789 A | 2/1989 | Muncheryan |
| 5,311,528 A | 5/1994 | Fujino |

(Continued)

FOREIGN PATENT DOCUMENTS

| CN | 1490907 A | 4/2004 |
| EP | 0 530 574 | 3/1993 |

(Continued)

OTHER PUBLICATIONS

Moon H-J et al., Efficient Diffusive Reflector-Type Diode Side-Pumped Nd: YAG Rod Laser with an Optical Slope Efficiency of 55%, Applied Optics, Optical Society of America, US, vol. 38, No. 9, Mar. 20, 1999, pp. 1772-1776. (ISR).

(Continued)

*Primary Examiner* — Ahmed Farah
(74) *Attorney, Agent, or Firm* — Collard & Roe, P.C.

(57) ABSTRACT

A monolithic, side pumped solid-state laser (1) comprising a laser resonator structure (3) comprised of a laser gain medium (2) having a longitudinal axis (L), wherein the laser resonator structure (3) comprises end faces (4) forming a linear optical path resonant cavity there between, at least one of the end faces (4) comprising at least partially reflecting laser mirrors (4a, 4b) in particular deposited thereon, the laser gain medium (2) comprising a side face (2a) for receiving pump light (5a) of a pump source (5), wherein the pump light (5a) is generated by a diode laser (5), and comprising a conductive cooler (6) comprising contact faces (6c) contacting the laser gain medium (2), and comprising a reflector (7) arranged opposite to the side face (2a) with respect to the longitudinal axis (L), wherein the laser gain medium (2) is a low gain material.

55 Claims, 16 Drawing Sheets

(51) Int. Cl.
- *A61B 18/20* (2006.01)
- *A61B 18/22* (2006.01)
- *H01S 3/0941* (2006.01)
- *H01S 3/042* (2006.01)
- *H01S 3/06* (2006.01)
- *H01S 3/02* (2006.01)
- *H01S 3/04* (2006.01)
- *H01S 3/094* (2006.01)
- *H01S 3/11* (2006.01)
- *H01S 3/08* (2006.01)

(52) U.S. Cl.
CPC .......... *H01S 3/094084* (2013.01); *H01S 3/025* (2013.01); *H01S 3/0405* (2013.01); *H01S 3/0621* (2013.01); *H01S 3/0627* (2013.01); *H01S 3/08072* (2013.01); *H01S 3/09408* (2013.01); *H01S 3/094057* (2013.01); *H01S 3/1118* (2013.01); *H01S 3/1608* (2013.01)

(56) References Cited

U.S. PATENT DOCUMENTS

| | | | | |
|---|---|---|---|---|
| 5,381,431 | A | 1/1995 | Zayhowski | |
| 5,394,412 | A | 2/1995 | Huignard et al. | |
| 5,394,413 | A | 2/1995 | Zayhowski | |
| 5,495,494 | A | 2/1996 | Molva et al. | |
| 5,636,239 | A | 6/1997 | Brusselbach et al. | |
| 5,642,370 | A | 6/1997 | Mitchell et al. | |
| 5,643,252 | A | 7/1997 | Waner et al. | |
| 5,646,773 | A | 7/1997 | Injeyan et al. | |
| 5,651,023 | A | 7/1997 | MacKinnon | |
| 5,761,233 | A * | 6/1998 | Bruesselbach et al. | 372/72 |
| 5,868,731 | A | 2/1999 | Budnik et al. | |
| 5,908,416 | A | 6/1999 | Costello et al. | |
| 5,928,220 | A | 7/1999 | Shimoji | |
| 5,947,957 | A | 9/1999 | Morris | |
| 6,219,361 | B1 | 4/2001 | Guch, Jr. et al. | |
| 6,224,590 | B1 | 5/2001 | Daikuzono | |
| 6,251,102 | B1 | 6/2001 | Gruzdev et al. | |
| 6,330,259 | B1 * | 12/2001 | Dahm | 372/35 |
| 6,366,596 | B1 | 4/2002 | Yin et al. | |
| 6,373,864 | B1 | 4/2002 | Georges et al. | |
| 6,377,593 | B1 | 4/2002 | Peterson et al. | |
| 6,395,000 | B1 | 5/2002 | Mitchell et al. | |
| 7,118,563 | B2 | 10/2006 | Weckwerth et al. | |
| 7,149,231 | B2 * | 12/2006 | Afzal et al. | 372/10 |
| 2003/0026312 | A1 | 2/2003 | Clayton et al. | |
| 2004/0066805 | A1 * | 4/2004 | Afzal et al. | 372/10 |
| 2004/0076212 | A1 | 4/2004 | Nunokawa et al. | |
| 2004/0101004 | A1 * | 5/2004 | Mukaihara et al. | 372/34 |
| 2004/0101015 | A1 | 5/2004 | Butterworth | |
| 2007/0060917 | A1 * | 3/2007 | Andriasyan | 606/10 |
| 2007/0071059 | A1 | 3/2007 | Afzal et al. | |
| 2007/0143769 | A1 | 6/2007 | Bu et al. | |
| 2008/0208297 | A1 | 8/2008 | Gertner et al. | |
| 2009/0304040 | A1 * | 12/2009 | Oron et al. | 372/72 |
| 2010/0195679 | A1 | 8/2010 | Kroupa et al. | |

FOREIGN PATENT DOCUMENTS

| | | |
|---|---|---|
| EP | 0 743 725 | 11/1996 |
| EP | 0 801 449 | 10/1997 |
| FR | 2 670 623 | 6/1992 |
| JP | 1 205484 | 8/1989 |
| JP | 5-335662 | 12/1993 |
| JP | 11 284253 | 10/1999 |
| JP | 2000-12932 | 1/2000 |
| WO | WO 96/28212 | 9/1996 |
| WO | WO 2004/034523 | 4/2004 |
| WO | WO 2006/111199 | 10/2006 |
| WO | WO 2006/111200 | 10/2006 |
| WO | WO 2006/111429 | 10/2006 |
| WO | WO 2006/111526 | 10/2006 |
| WO | WO 2007/074400 | 7/2007 |
| WO | WO 2007/143769 | 12/2007 |
| WO | WO 2008/049903 | 5/2008 |
| WO | WO 2009/150210 | 12/2009 |

OTHER PUBLICATIONS

Peng et al., Picosecond Laser Amplification System with 93 W High Average Power, Optics Communications, North-Holland Publishing Co., Amsterdam, NL, vol. 281, No. 10, Feb. 5, 2008, pp. 2879-2882. (ISR).

International Search Report of PCT/EP2010/003586, date of Mailing Oct. 1, 2010.

International Preliminary Report on Patentability of PCT/EP2010/003586, dated Sep. 5, 2011.

* cited by examiner

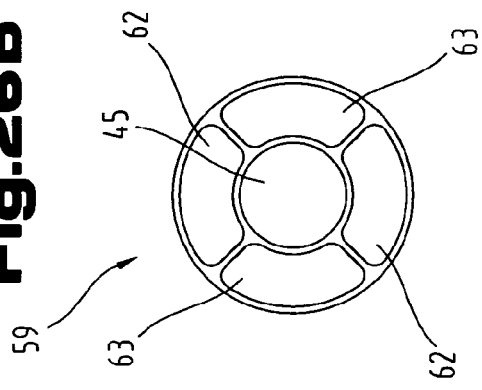
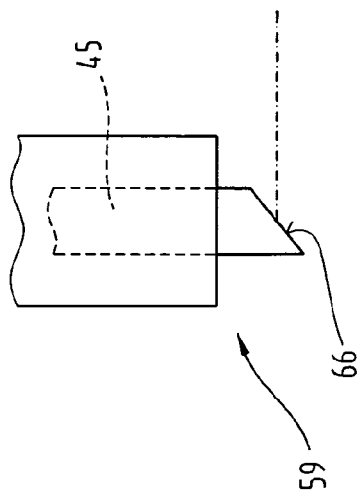
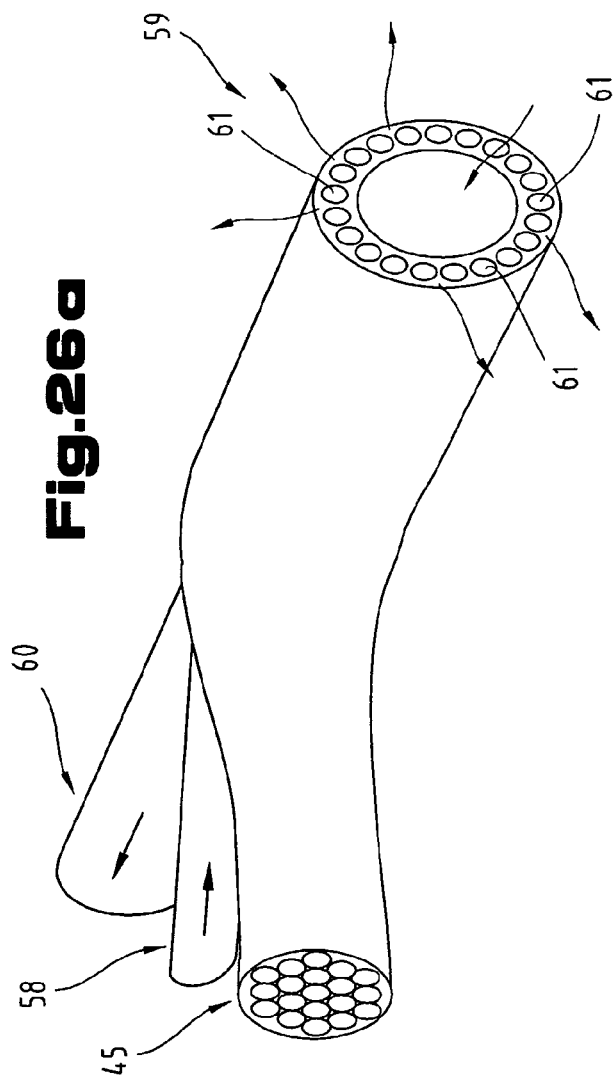
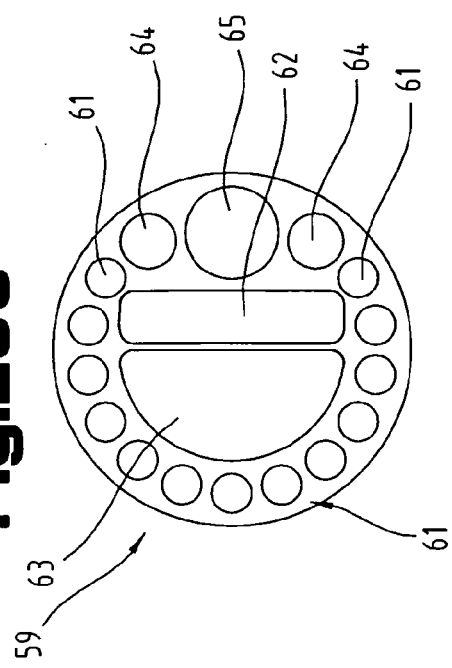

US 9,368,931 B2

MONOLITHIC, SIDE PUMPED SOLID-STATE LASER AND APPLICATIONS THEREOF

CROSS REFERENCE TO RELATED APPLICATIONS

This application is the National Stage of PCT/EP2010/003586 filed on Jun. 15, 2010, which claims priority under 35 U.S.C. §119 of PCT/EP2009/057398 filed on Jun. 15, 2009, PCT/EP2010/050458 filed on Jan. 15, 2010, and PCT/EP2010/051825 filed on Feb. 13, 2010 and under 35 U.S.C. §119(e) of U.S. Provisional Application Ser. No. 61/397,656 filed on Jun. 15, 2010, the disclosures of all of the above applications are incorporated herein by reference. The international application under PCT article 21(2) was published in English.

FIELD OF THE INVENTION

This invention relates to a monolithic, side-pumped solid-state laser. The invention further relates to a method for operating a monolithic, side pumped solid-state laser. The invention further relates to treatment devices.

BACKGROUND OF THE INVENTION

Diode pumped lasers have grown in usefulness, particularly in industrial, medical and military applications. Diode pumped lasers are particularly useful, because diode pumps are power efficient, all solid-state and long lived. These result in laser systems that are lighter, more efficient and typically not water cooled, as compared to similar flash lamp pumped solid-state lasers.

In general, end-pumped or side pumped solid-state laser configurations are known. Q-switched lasers or monolithic lasers are configurations such as those described in U.S. Pat. Nos. 5,394,413; 5,381,431; 5,495,494; 5,651,023 and 6,373,864 B1. Disadvantages of such designs are, inter alia, limitations regarding the maximal pulse energy. In addition Q-switched lasers are able to only produce pulses of very short duration.

U.S. Pat. Nos. 6,219,361 B1 and 6,377,593 B1 describe side pumped designs, where the beam path takes an internal zig-zag path, such design lengthening the pulse duration and increases manufacturing difficulty and cost.

In diode side-pumped geometries, the gain media is typically either a rod or a slab. Slab geometries have typically been used in conductively cooled laser systems with one side of the slab attached to a thermal heat sink, and with the opposing face used for the introduction of pump light. Side pumped slabs can employ various techniques such as utilizing a so called "zig-zag" optical path, as for example disclosed in US 2007/0060917, FIG. 2b. Zig-zag slabs, however, are difficult to fabricate owing to tight optical tolerances and are therefore more difficult to produce in large quantities than straight through slab embodiments, and are therefore more expensive to produce.

Document WO2004/034523 discloses a monolithic, side pumped, passively Q-switched and not water cooled solid-state laser that includes a laser resonator structure, and that includes a laser gain medium having an output face bonded to a passive Q-switch. The gain medium has a side face for receiving pump light. The pump light is generated by a diode laser array. One disadvantage of this solid-state laser is that the average power is limited. Another disadvantage of this solid-state laser is that thermal effects arise during operation. In addition Q-switched lasers are able to only produce pulses of very short duration.

Document US 2007/0060917 discloses in FIGS. 1b and 2a a MIR (mid-infrared) diode side pumped solid-state laser that includes a laser resonator structure were gain switched pulse can be emitted (FIG. 5c). One disadvantage of this solid-state laser is that the power of the generated laser light is limited and low.

Document U.S. Pat. No. 6,366,596 B1 discloses a diode side pumped OPO laser that generates, inter alia, MIR (mid-infrared) radiation. Although the wavelength can be tuned in a wide range in the MIR wavelength region, the disadvantage of such lasers is the short pulse duration in the one and two digit nanosecond region with high power densities (intensities) or if the laser pulse lengths are in the microsecond region the laser pulse intensity is very low. In addition such lasers are complex, require optical elements with various optical coatings, and are thus very expensive. Another disadvantage is that such lasers are not robust against shock and vibration, and that the large number of critical components increases the likelihood of a system failure.

Documents U.S. Pat. No. 5,642,370; U.S. Pat. No. 5,643,252; U.S. Pat. No. 5,868,731; U.S. Pat. No. 5,908,416; U.S. Pat. No. 5,947,957; U.S. Pat. No. 6,251,102 B1 and U.S. Pat. No. 6,395,000 B1 disclose side pumped solid-state lasers working in the mid-infrared wavelength region. In general such solid-state lasers are used for biological tissue ablation. Some of these lasers are battery powered and so called self contained, delivering single laser pulses followed by a few seconds charge time of the capacitors in the high voltage power supply.

It is therefore an object of the present invention to provide a side-pumped solid-state laser device for generating high power laser light pulses. It is a further object of the present invention to provide an inexpensive, robust and reliable laser device. It is a further object of the present invention to provide a high performance operating laser device, in particular to provide laser light having high pulse energy and/or high power and in particular allowing high pulse repetition rate in a broad working range. It is a further object of the present invention to provide a laser device suitable to be used in the medical field, in particular with a wavelength in the mid-infrared (MIR) range of between 1700 nm to 3200 nm, and/or in particular suitable for treating, cutting or ablating biological tissue. It is a further objective of the invention to provide a treatment device that enables a user to perform high powered laser pulse treatments, where the treatment device is easy to handle, especially a maintenance friendly embodiment should be achieved. Furthermore it is an objective to find a treatment device that allows a high powered laser pulse treatment off site a specialised treatment unit.

SUMMARY OF THE INVENTION

This problem is solved with a monolithic, side pumped solid-state laser as described herein. The problem is further solved with a method for operating a monolithic, side pumped solid-state laser as described herein.

The problem is in particular solved with a monolithic, side pumped solid-state laser comprising a laser resonator structure comprised of a laser gain medium having a longitudinal axis L, wherein the laser resonator structure comprises end faces forming a linear optical path resonant cavity there between, at least one of the end faces comprising at least partially reflecting coatings deposited thereon, the laser gain medium comprising a side face for receiving pump light of a pump source, wherein the pump light is generated by a diode laser, and comprising a conductive cooler comprising contact faces contacting the laser gain medium, and comprising a reflector arranged opposite to the side face with respect to the longitudinal axis L.

The problem is further in particular solved with a monolithic, side pumped solid-state laser comprising a laser resonator structure comprised of a laser gain medium having a longitudinal axis L, wherein the laser resonator structure comprises end faces forming a linear optical path resonant cavity there between, at least one of the end faces comprising at least partially reflecting laser mirrors in particular deposited thereon, the laser gain medium comprising a side face for receiving pump light of a pump source, wherein the pump light is generated by a diode laser, and comprising a conductive cooler comprising contact faces contacting the laser gain medium, and comprising a reflector arranged opposite to the side face with respect to the longitudinal axis L, wherein the laser gain medium is in particular a low gain material.

The problem is further in particular solved with a method for operating a monolithic, side pumped solid-state laser comprising a laser resonator structure comprised of a laser gain medium having a longitudinal axis L, wherein pump light is fed through a side face into the laser gain medium, wherein part of the pump light is exiting the laser gain medium at an opposite side face as an exiting pump light, and wherein the exiting pump light is reflected such that a reflected pump light is reentering the laser gain medium at the opposite side face.

The diode side pumped solid-state laser disclosed in Document US 2007/0060917 generates low quality laser light respectively of low intensity. On the other hand, it has been found out that the laser light needs a certain level of intensity to highly efficient ablate biological tissue. It is further known that diode side pumped solid-state lasers emit less pulse energy than flash lamp pumped solid-state lasers. The monolithic, side pumped solid-state laser according to the invention uses several technical features to improve the intensity, respectively the beam quality, of the laser light. First of all a laser gain medium having a cross sectional area of less than 7.5 mm$^2$ is used, whereas the cross sectional area is a surface inside the laser gain medium perpendicular to the laser propagation direction and in case of plane laser mirrors, parallel to them. If the laser gain medium has the shape of a rod, with a circular or elliptical cross section, this means that the rod has a diameter of less or equal 3 mm, preferably less or equal 2 mm, most preferably less or equal 1 mm. The advantage of a rod having such a small diameter respectively having such a small cross sectional area is the fact that less pump power is required to achieve a certain power density inside the laser gain medium that is required to start the laser oscillation. Furthermore a laser rod with such small cross sectional area act like an aperture inside the laser cavity and induce losses for the higher transversal laser modes respectively improve the quality of the laser light. Only by using a rod with such a small cross sectional area it is possible to create sufficient power density inside the laser gain medium, whereby the pump light is generated by a semiconductor laser. Assuming the laser rod would have a diameter of 4 mm, then the cross sectional area would increase to about 12.5 mm$^2$, which is about double the cross sectional area of the 3 mm rod. The 4 mm rod needs about two times the pump power to achieve the same power density than the 3 mm rod. It is therefore a very important advantage to limit the cross sectional area of the laser gain medium to less than 7.5 mm$^2$. In a preferred embodiment the diode laser pump power within the laser active medium is between 20 and 500 W/mm$^3$.

In a preferred embodiment the intra cavity laser intensity (within the laser active medium) is between 5 kW/cm$^2$ and 10 MW/cm$^2$ and more preferably between 10 and 100 kW/cm$^2$.

A further advantageous measure to increase the efficiency of a laser is to optimize the percentage coupled out of the laser. The lower the stimulated emission cross section respectively the gain of the laser gain medium is, the lower must be the percentage coupled out of the laser in order to operate the laser efficiently. This is equivalent with a high intensity inside the laser cavity, which is advantageous to start the laser oscillation. Therefore it is advantageous to operate a laser with a laser gain medium with low stimulated emission cross section with high intensities inside the laser cavity.

A further advantageous measure to increase the intensity within the laser gain medium is to use an output coupler that has a reflectivity in the range of between 92.5% to 99%. A further advantageous measure to increase the intensity within the laser gain medium is to reduce cavity losses. It is a disadvantage of solid-state lasers such as disclosed in document US 2007/0060917 that the use of a discrete laser cavity causes optical losses through media transitions from the laser gain medium to air and from air to the laser mirrors due to reflection and absorption losses of laser light on these transitions. Since the used laser media are low gain laser materials, these additional losses prevent such known laser systems from efficient operation. Another disadvantage of laser cavities especially working in the mid infrared (MIR) wavelength region of 1700 nm to 3200 nm is that dust or humid air between the laser gain medium and the laser mirrors strongly reduce efficiency of the laser system or almost stop the laser cavity from emitting laser light due to the strong water absorption of the emitted laser light. This causes additional losses and further reduces intensity within the laser gain medium.

A further advantage measure to improve the laser performance is to control the laser gain medium temperature. Laser rods with such small diameters exhibit a better surface to volume ratio and thus can be cooled or heated more efficiently which reduces thermally induced distortions of the laser beam quality. A further advantage resulting from the improved thermal performance is the increased output power and increased optical to optical efficiency.

A further advantageous measure to optimise the laser output beam quality is to symmetrically cool the laser active gain medium. Due to the fact that the laser gain medium in WO2004/034523 is not cooled symmetrically, the beam profile is not homogeneous and therefore the beam parameter product M$^2$ is bad which leads to poor focusability. The symmetrical cooling of the laser active gain medium according to the invention therefore leads to a homogeneous beam profile and a symmetrical and collinear thermal lens with the longitudinal axis of the active medium. This ensures that the laser always oscillations along this axis and hence is a necessary feature to guaranty stable operation over a wide range of parameters like pump power, repetition-rate and duty-cycle.

A further advantage of the solid-state laser according to the invention is that the manufacturing costs are low and that little maintenance is required. This strongly improves market acceptance. This advantage is achieved by reducing the number of needed optical elements and/or the number of adjustable optical elements or laser cavities. Especially adjustable optical elements or laser cavities in hand held or movable laser based medical and non medical devices have been the cause for market failure and expensive product call-backs or at least high maintenance costs. A solid-state laser according to the invention is highly shock and vibration proof as well as stable even after quick changes of environment conditions like e.g. temperature, humidity and ensures a highly stable and constant laser output power which is required by laws and regulations for laser based medical devices. Laser designs produced according to conventional methods suffer from robustness and usually self-disadjust. In addition a decrease in laser output power might occur, caused by temperature, mechanical stress (shock, vibration), dust on optics and so on. Such devices have to be repaired, optics have to be cleaned and laser cavities have to be realigned on a regularly basis which causes high maintenance costs.

A further advantage of the solid-state laser according to the invention is that the design can be highly miniaturized due to the highly efficient and also short laser cavity. This allows implementing the solid-state laser in device parts which in the past could not include a high power solid-state laser. One example would be the implementation of a mid infrared solid-state laser with e.g. up to 5 W in a so called self contained or handheld wireless device such as disclosed in U.S. Pat. No. 7,118,563. Today only a diode laser in the near infrared (780-1400 nm) can be used in such devices. One advantage of the invention is, that battery powered self contained devices can now be provided with mid-infrared solid-state lasers. In addition, such devices can also be light weighted, e.g. less than 1 kg. Other new devices comprising a laser may be build which are smaller and less power consuming. It could be even thought about a device consisting of (i) a table-top part containing a power supply, a cooling unit and eventually a control unit, and (ii) a hand held unit containing the solid-state laser, eventually beam shaping optics, beam deflection means and maybe also a control unit. The hand held unit could be detachable for maintenance reasons and could be sent within a small light weight package to the device manufacturer. Before shipping the device to the manufacturer the device owner can inform him and could be provided with a temporary hand held unit prior to sending back his hand held unit via ordinary mail for service reasons. The exact procedure would be as follows: a) For service reasons the base station could inform the user that a service is upcoming and that he should call the device manufacturer for a temporary exchange of the handheld device unit or handpiece. b) The device owner or user sends an oral or written message to the device distributor or manufacturer. c) The device distributor or manufacturer sends a parcel with a temporary exchange handheld device unit or handpiece. d) The device owner or user just exchanges the handheld device within a very short time due to an easy plug connector so he has no device downtime. e) A parcel service takes the handheld device unit or handpiece for service to the service centre or to the device manufacturer where it is repaired and serviced. f) After the completion of this service procedure the handheld device unit or handpiece is sent back to the device owner or user. g) The device owner or user exchanges the handheld device unit or handpiece again and sends back the temporary handheld device unit or handpiece. No more expensive travelling of service personal is necessary and no more expensive shipping of heavy devices with fragile optics is needed any more. Expensive local service centres are not necessary any more. The user doesn't have to reserve a room for the service personnel and wait until the device is repaired. In addition to that handheld device s with other functions (pulse energies, wavelengths, additional measurements, ... ) or treatment optimized handheld devices can be attached to the basis station. All these advantages lead to a very economic product and satisfied customers. All above mentioned advantages are also valid for self-contained devices, where no tabletop unit/base station is required.

In a further advantageous embodiment the pump light is guided such that there is an about homogenous distribution of the pump light in the laser gain medium 2. Most advantageously this is achieved by a pump light reflector arranged opposite to the side face with respect to the longitudinal axis of the laser gain medium. This arrangement allows the pump light entering the laser gain medium from the side face to cross the laser gain medium, to exit the laser gain medium, and being reflected by the pump light reflector, so that the reflected light again enters the laser gain medium. This embodiment creates a homogenous light distribution within the laser gain medium. The advantage of such a homogenous light distribution is that it results in a much better laser mode compared to conventional systems. This laser mode can have a beam parameter product $M^2$ between 1 and 25 which is the key to a very well focusable laser beam.

A further advantage of the small cross sectional area of the laser gain medium is that the laser beam can be focused to a smaller diameter. Known flash lamp pumped lasers or diode pumped lasers with laser gain media cross sectional areas allow the laser beam to be focused to 300 to 500 µm. The laser gain media used in the solid-state laser according to the invention allows the laser beam to be focused to about 100 to 250 µm. This allows increasing the intensity of the laser beam in the focus.

A further advantage of the solid-state laser according to the invention is that the laser beam with such a small cross sectional area can now be transmitted high efficiently through thin and thus inexpensive light fibers. A further advantage of the invention is, that the transmission of the laser beam into the fiber is more efficient because the better the laser beam quality the more efficient the incoupling into the fiber which is equivalent to reduced losses.

A further advantage of the solid-state laser according to the invention is that it does not comprise adjustable optical elements such as for example laser mirrors or flash lamps. The solid-state laser according to the invention is therefore robust against disadjustment caused by shock events, vibration or disadjustment over time caused by thermal effects. A further advantage is that the solid-state laser overcomes the loss of power over time, which is typical for flash lamps.

A further advantage of the solid-state laser according to the invention is that the maintenance expenses are low. Because of the laws and regulations for laser based medical devices, a change in optical output power is allowed only within small ranges. Known solid-state lasers therefore required expensive maintenance on a periodical basis or required complex control mechanisms to fulfil such laws and regulations.

In a preferred embodiment the present invention provides a laser device suitable to generate laser light to be used in the medical field, in particular suitable for treating, cutting or ablating biological tissue including hard tissue. Background information regarding laser devices and treating or ablating biological tissue are disclose in the following patent applications, all of them incorporated by reference: WO2006/111526, WO2006/111200, WO2006/111199, WO2006/111429 and WO2008/049903. In a preferred embodiment the laser device according to the invention is used for treating, cutting or ablating biological tissue including hard tissue. It has been found out that most advantageous biological tissue ablation is achieved with laser pulses having a pulse length of between 1 µs and 15 µs and having an intensity of between $10^3$ W/mm$^2$ and $10^8$ W/mm$^2$. Such laser pulses allow a highly efficient ablation of biological tissue, with reduced destruction, for example reduced thermal damage like e.g. denaturation, coagulation, carbonization of the adjacent biological tissue. It has been found out that a certain level of intensity is necessary to efficiently ablate biological tissue and that a certain level of intensity is even more important than high pulse energy. It has been found out that a pulse of high pulse energy, whereby the high pulse energy is achieved by a pulse of long duration, is much less efficient than a pulse having a certain intensity of between $10^3$ to $10^6$ W/mm$^2$ for e.g. soft tissue and $10^5$ to $10^8$ W/mm$^2$ for hard tissue. Therefore generating laser light having an intensity of between $10^3$ W/mm$^2$ and $10^8$ W/mm$^2$ is most preferred for ablating or cutting biological tissue, whereby the pulse length of the laser light most preferably is in the range of between 1 µs and 15 µs, and less preferably is in the range of between 15 µs and 200 µs. Pulses shorter than 1 us e.g. produced by Q-Switched lasers or OPO lasers destroy tissue in a mechanical manner through shock waves, tearing cells apart from their natural bond. To achieve an intensity of the laser light of between $10^3$ W/mm$^2$ and $10^8$ W/mm$^2$ on the target such as the biological tissue, the size of the laser light hitting the target may be shaped using beamshaping, in particular by using lenses.

According to one aspect of the invention, a solid-state laser and an apparatus comprising the solid-state laser is disclosed, suitable for cutting or ablating biological tissue. The solid-state laser comprises an optical cavity; a gain medium disposed within the optical cavity; a semiconductor laser optically aligned to light pump the gain medium to generate laser light, wherein the generated laser light has a wavelength and an intensity suitable for cutting and ablating biological tissue.

In accordance with one aspect of the present invention, a method of cutting or ablating biological tissue including hard tissue is disclosed, comprising the steps of providing a gain medium, a semiconductor laser, and an optical cavity; placing the gain medium and the semiconductor laser within the optical cavity so that the semiconductor laser is optically aligned to pump the gain medium; activating the semiconductor laser to optically pump the gain medium and generate laser light; and directing the laser light onto the biological tissue such as soft, medium hard or hard tissue to cut or ablate the biological tissue.

In one embodiment at least one of pulse width, pulse shape, repetition rate, pulse intensity and pulse energy of the laser beam can be modulated, which allows to modulate the characteristics of individual cuts or pores created in the biological tissue as well as the ablated depth of biological tissue per pulse.

The laser for treating or ablating biological tissue having a wavelength between 1700 nm and 3200 nm. Most preferred a wavelength of about 2950 nm is used because this is a major local maximum in the water absorption spectrum in the MIR (mid infrared) range.

A solid-state laser according to the invention preferably generates a laser beam having a diameter between 0.5 mm to 2.5 mm, and more preferably having a diameter between 0.5 mm and 1 mm.

Such a solid-state laser preferably has a pulse temporal width between 1 µs and 500 µs, in particular between 1 µs and 200 µs, and most preferably between 1 µs and 15 µs.

Such a solid-state laser has a laser pulse energy between 0.1 mJ and 100 J, in particular between 1 mJ and 5 J.

Such a solid-state laser being able to be focused to a spot, having an intensity of the laser radiation between 1 W/mm$^2$ and $10^8$ W/mm$^2$, in particular between $10^3$ W/mm$^2$ and $10^7$ W/mm$^2$.

Important design parameters of a crystal are: pump power and crystal diameter, important laser material parameters are: stimulated emission cross section, lifetime and photon energy.

For the laser action it is not important in which way the laser active material is supplied with energy. Namely it is not important, if the pump light enters from the side or collinear or if the pump is a laser diode or a flash lamp etc. The starting point of the invention is that the laser active material is full of energy, more specific is already pumped by the laser diode. In the case of Er:YAG this means that the pump light of about 980 nm has entered the crystal and the total supplied energy is E_pump, which is transferred to the laser active ions. In this process energy is lost and for laser action just the following amount is available E_stored=E_pump*(Wavelength_pump/Wavelength_laser)=e.g. for Er:YAG ca. E_pump*980/2940=0.33*E_pump The important cross section A of the laser is perpendicular to the laser axis—in the present case the laser crystal end faces, which is directly proportional to the diameter d.

From the material point of view, the stimulated emission cross section, the photon energy and the lifetime of the laser transition are important. The lifetime is important for pumping of the crystal, because one has to get the energy into the crystal to reach the laser threshold. When the laser action starts, the lifetime of the laser active ions is determined by the out coupling and other cavity parameters and not exclusively by the lifetime of the upper laser level anymore. Since the focus is kept on the situation, where the energy is already inside the crystal, one can ignore the lifetime. The situation is very similar to a laser amplifier, where the laser crystal is pumped and afterwards a pulse to amplify is send through.

Therefore just the photon energy of the laser transition and the stimulated emission cross section remain as material parameters. The photon energy is the difference between the upper and lower laser level and the stimulated emission cross section is the area around one laser active ion, where a photon has to pass in order to stimulate the emission of another laser photon.

In laser amplifiers the saturation fluence is the main design parameter, which defines the energy which has to be pumped into a crystal in order to fill the whole crystal area A with active laser ions ready to supply a laser photon. In other words every photon, which enters the crystal, is highly likely to stimulate the emission of another photon.

$$F_{sat} = \frac{h\nu}{\sigma_{em}} = x \frac{E_{stored}}{A} = x \frac{E_{pump} \frac{wl_{pump}}{wl_{laser}}}{\pi \left(\frac{d}{2}\right)^2}$$

This equation combines the material parameters photon energy and stimulated emission cross section with the pump energy and the crystal diameter (proportional factor x—smaller is better). For easier understanding x=1 and therefore $$\frac{h\nu}{\sigma_{em}} = \frac{E_{stored}}{A}$$

The photon energy is fixed by the laser wavelength and the smaller the stimulated emission cross section the larger the whole expression becomes. In order to maximize the right side—either more energy needs to be pumped into the crystal or the area A is reduced by reducing the crystal diameter d or both at the same time.

In total a laser material with a low emission cross section can only be operated by very strong pumping of a small diameter laser crystal.

Of advantage is an embodiment, where in the pump light is fed through a side face into the laser gain medium, wherein 30 to 70% and preferably 30 to 50% of the pump light is exiting the laser gain medium at an opposite side face as an exiting pump light, and wherein the exiting pump light is reflected by the reflector, such that a reflected pump light is re-entering the laser gain medium at the opposite side face. Using a specific wavelength different form a wavelength at an absorption peak of the gain material has the advantage, that incident pump light is only partially absorbed by the laser gain medium and therefore an amount of 30 to 70% and preferably 30 to 50% of the incident pump light exits the laser gain medium and is reflected backwards to the laser gain medium, where it is further absorbed in total to 50 to 91% and preferably to 75 to 91%. Therefore a uniform light distribution within the laser gain medium is achieved, thus resulting in a uniform, Gaussian like, energy distribution within the emitted laser beam. The reflector may be embodied as having a high reflection coefficient, reflecting almost the entire incident light, furthermore it may be reflecting partially or diffuse, in order to enhance the uniform illumination of the laser gain material.

The wavelength/wavelength region shift of the pump source relative to the absorption maximum depends on the crystal diameter and the dopant concentration of the crystal material and is chosen in a way that the crystal diameter is equal one absorption length. The absorption length is defined as the length of the laser material after 63.2% of the pump radiation entering the laser material is absorbed. These measures lead to an optimized pump light distribution/to an optimized, more homogenous illumination within the crystal. If the pump light wave-length/wavelength region would be chosen at the absorption maximum, the pump light would be absorbed in a crystal with e.g. 2 mm in e.g. 1 mm and the remaining crystal is not illuminated which dramatically decreases the laser beam quality. A simplified equation is like follows:

Diameter of crystal: X
Absorption coefficient: Alpha
Condition: X*Alpha=1
Law of Absorption:

Absorption within crystal=exp(−X*Alpha)=exp(−1) =0.632. Each laser material has a specific absorption coefficient Alpha, which depends on the wavelength and therefore this equation is valid for all laser materials in this pump geometry.

A pump source that is embodied as laser diode array, which is arranged parallel to the longitudinal axis has the advantage that the laser gain medium can be provided with pump light, distributed a long its length. It is preferred that the length of the pump source is at least 30% of the length of the laser gain medium. This embodiment is aimed to provide a uniform illumination of the laser gain material and to provide sufficient pump light energy in order to start the lasing of the low gain material.

The low gain material is characterised that it is a laser gain media with a stimulated emission cross section equal or less than that of Er:YAG namely $<=3.0*10^{-20}$ cm$^2$. This laser gain medium distinguishes the solid-state laser according to the present invention from high efficiency laser systems, where a high gain laser material like Nd:YAG with a stimulated emission cross section of $28*10^{-20}$ cm$^2$ is used, in order to get a high optical and electrical efficiency factor. With a high gain material, a much greater amount of light can be coupled out of the optical resonator for treatment issues.

Due to the robust embodiment of the solid-state laser, especially due to the arrangement of the laser gain medium surrounded and held by the conductive cooler, the laser can withstand an appealing force of at least 100 G. This allows the laser to be shipped without requiring a specialized shipment procedure. In particular it is not required to perform maintenance work on site, as the laser can be shipped to a maintenance station.

Due to the very good laser beam quality it is also easily possible to combine multiple laser units either in series (one after the other, in line and collinear to the laser beam propagation axis) or via mirrors, stair mirrors, lenses and other coupling units known in the art. The combination of multiple lasers allows increasing the maximum and/or average output power but also increasing repetition rate by factors of a single laser unit. High output powers would allow to treat materials that contain very low amounts of water or hydroxyls (OH-bonds) or create very high shock waves and big cavitation bubbles or even would allow plasma generation. Ideally the lasers would be phase locked so that the beam can be coherently combined A monolithic design of the lasers is characterised in that a laser high reflector is deposited directly on the gain medium, and an output coupler is deposited directly on the opposite end on the gain medium, Due to the low gain of the introduced laser material, an arrangement of the laser mirrors offset to the end faces of the laser material is quite difficult, as there would hardly occur lasing, because of the losses when there is a media change from the laser material to free air, and then to the mirror material and backwards.

One objective of the invention is solved by a treatment device which comprises a solid-state laser according to the present invention which is arranged in a housing, and whereby the emitted laser beam of the solid-state laser is directed to a handheld device by a light guiding element within a flexible hose. The handheld device comprises an outlet port for the ending of the light guiding element, for directing the laser beam to the target surface. The flexible hose comprising the light guiding element, thus allowing a distributed arrangement of the laser source and the treatment operation device, which is the handheld unit, where a high energy output laser device delivers its output power via the light guiding element to the treatment device.

As the pump light of the solid-state laser requires a high amount of electrical energy in order to create pump light with a sufficient energy density, the power supply must be able to provide a high amount of electrical energy in a very short period of time. This requires either very powerful power supply, or according to an embodiment, a power supply with a high current capacity buffer. With this embodiment it is possible to charge the buffer continuously over a sufficiently long time period, and discharge the buffer in a very short time period, providing a high current power to the pump light source.

For using the treatment device e.g. in medical applications, it is very useful to have pressurized gas available at the handheld device, therefore according to one embodiment, the housing of the treatment device comprises a device for generating a pressurize gas, in particular with positive and/or negative pressure, relative to the ambient pressure. Pressurized gas as used herein, incorporates especially air and all mixtures of process gasses that can be used to improve the ablating and/or ensure an unaffected ablating, by e.g. removing oxygen from the treatment area.

As similar embodiment is that the housing comprises a device for generating a pressurized liquid. As the laser beam ablates material by a thermal ablation method, it could be useful to purge and/or cool a target area, therefore it is of advantage to have a liquid available at the handheld device.

The flexible hose will therefore comprise ducts for delivering pressurized liquid from the device in the housing to the handheld device, or the flexible hose will comprise a duct for providing the pressurized gas to the handheld device. Using a pressurized gas with a positive/relative pressure could be used e.g. for providing an inert gas cap around the treatment point, especially for avoiding an oxygen atmosphere around the operation area of the laser beam on the target surface. Using a gas with a negative relative pressure could be used for suctioning material away from the operation area of the laser beam on the target surface. As the laser beam will ablate material from the target surface this has to be removed from the target area in order for a proper operation of the laser. According to the embodiment this material can be sucked away and transported via duct in the flexible hose to a disposal unit or to a disposable unit in the housing, providing a clean target area.

An embodiment, where the housing comprises a detachable connector means has the advantage that every usage of the treatment device, especially every usage of the handheld device, can be performed with a new handheld device and flexible hose. For applications with harmful materials it is possible that the handheld device and the flexible hose become contaminated and need to be replaced. Such an embodiment is suitable for cheap optical light guiding elements, e.g. light guiding elements based on silicon oxides, where it is cheaper to dispose the light guiding element in the hose together with the handheld device, than to perform a thorough cleaning. Otherwise the entire handheld device together with the flexible hose can be cleaned or sterilized.

Having a very expensive optical light guiding element arranged in the hose, e.g. made of sapphire, germanium oxide, zirconium fluoride, ceramic fibers, ceramic glass fibers, selen or tellur containing fibers, or in general fluoride based or ceramics based or crystalline material based fibers, it is important to keep the optical light guiding element and change or clean only the handheld device. According to one embodiment, the handheld device comprises a detachable connector means allowing the handheld device to be disposed after every usage. According to a further embodiment, the detachable connector means could be arranged at the housing, thus enabling the handheld device together with the hose to be disconnected from the housing. A further embodiment could be that the hose comprises a detachable connecter on both ends, thus allowing an individual disconnection of the handheld device and the flexible hose. This could be suitable for performing different cleaning tasks, e.g. for sterilizing the handheld device in an autoclave unit, the flexible hose may be submerged in a disinfection solution.

According to the present invention the handheld device comprises an outlet port for the ending of the light guiding element, for directing the laser beam to the target surface. According to an embodiment, the handheld device comprises a beam formation and/or deflection unit, thus allowing the laser beam, provided by the optical light guiding element to be formed, e.g. to provide a specific energy density distribution, or for deflecting the laser beam to a specific point within the target area, or for providing a specific movement pattern within the target area. The laser beam emitted to the ending of the light guiding element enters the beam formation and/or deflection unit, is there within accordingly treated, and leaves the handheld device via the outlet port.

In order for a handing the treatment possibilities the handheld device further comprises a sound transducer in particular and ultrasonic sound transducer. A laser operates mainly by generating a high temperature pulse within the target region, thereby ablating material. Having a sound transducer available at the handheld device, which directs the generated sound pulses via a guidance means to e.g. a tip in the outlet port, provides mechanical energy for ablating material together with the thermal ablating done by the laser. The laser part could be used for the critical areas where surrounding tissue must not be damaged and the ultrasound part could be used for high speed removal of less critical areas.

For some applications it is useful to have multiple beams available at the target area, so according to one embodiment, the handheld device comprises a light guiding element splitting unit that feeds the laser beam, provided by the solid-state laser via the optical light guiding element, into multiple laser beams. This can be done e.g. via a splicing of the optical light guiding element, a diffractive optics, micro lens optics, stair mirrors, compound parabolic concentrators, or an inversed used multi-fiber concentrator. A further advantage of this embodiment is that on the media change interface, where the laser enters the target area, due to the high amount of light energy, cavitation bubbles can occur, with reduced power density available at the target area. Having the laser beam split up into multiple laser beams, reduces the power density per laser beam and therefore reduces the chance for generating these cavitation bubbles. As an effect, no energy is wasted into unwanted cavitation and more energy is directed to the target area.

As the target area to be treated is usually quite small, so that an optical evaluation of the treatment process by the operator is quite difficult, so according to one further embodiment, the handheld device comprises an optical imaging means. This optical imaging means can be e.g. an imaging sensor like a CCD camera, arranged in or around the outlet port, directed towards the target area. It is further possible to have one optical light guiding element that is directed towards the target area and delivers the image to an image capturing means, arranged in the handheld device or in the housing, where for the letter, the flexible hose further comprises another light guiding element for transporting the acquired image from the handheld device to the housing. In another embodiment, two optical imaging means arranged could be arranged in the handheld device, allowing a stereographic captioning of the target area and providing the operator of the treatment device with a 3D image of the target area. A further embodiment could be that the handheld device, especially the outlet port, comprises an illumination means for illuminating the target area.

According to a further embodiment, the handheld device comprises a radio frequency transmitter preferably emitting a radio frequency in the range from 50 kHz to 5 MHz. With this embodiment, further treatments may be possible in that radio frequency, can be selected to penetrate the target material to a desired depth. Preferably the radio frequency transmitter is tuneable, so that an optimised application specific radio frequency can be transmitted to the target area. Furthermore the radio frequency transmitter comprises an antenna means, for directing the radio frequency to the tissue to be treated respectively to be ablated. The laser part could be used for the critical areas where surrounding tissue must not be damaged and the radio frequency part could be used for high speed removal of less critical tissue areas.

For supplying the various devices within the handheld device, the flexible hose comprises a power supply cable providing electrical energy from a power supply within the housing to the handheld device.

In order to control the emission of the laser beam to the target area, it is of advantage that the flexible hose comprises at least one data transmission line which e.g. connects a control unit and a handheld device, with a control unit and a housing. The control unit in the handheld device is embodied to perform user interactions, especially providing a control capability to the user, for controlling the operation of the laser. The control unit in the housing receives the commands from the control unit in the handheld device, and operates the laser accordingly. A data transmission line has the advantage that a various number of commands can be transmitted without requiring a large number of individual control lines.

The optical light guiding element can be embodied as a single fiber light guiding element, which has the advantage that the entire optical energy of the laser beam is transported within one single fiber, thus easing the coupling of the laser beam into the fiber and receiving the laser beam from the fiber, for directing it to the target surface.

According to a further embodiment, the optical light guiding element is embodied as multi fiber light guiding element, which has the advantage that the energy density within each single fiber is reduced and thus the optical stress to the fiber material is reduced and therefore chance of damaging the fiber, due to excess optical energy is reduced. Furthermore the risk of generating cavitation bubbles is reduced, as less optical energy is emitted from each fiber to the target area. Each of the single fibers can have the same function, transporting the laser beam from the solid-state laser to the handheld device, or individual fibers can be configured to perform different tasks. For example a fiber of a multi fiber optical light guiding element can be used for illumination purposes, another fiber can be used for sensing or analysing issues, in that it transports an image of the target area to an analysis module in the housing. Each of the individual fibers can be made of the same material, where in one embodiment different materials can be used for the individual fibers. This has the advantage that different wavelengths can be used, where the fiber materials are selected to provide an optimal light transport for the individual wavelength. Therefore it is possible to have one solid-state laser, which is tuneable to emit a laser beam in different wavelength, or multiple solid-state lasers, each emitting on a specific wavelength, or semiconductor lasers or even light sources like light emitting diodes, can be arranged in the housing and coupling their laser beam into a number of the individual fibers. Using different wavelengths has the advantage that more materials can be treated as the wavelength has to be adjusted to the material to be treated.

As used herein the term fiber refers to any kind of optical waveguide that is capable of guiding light at one, or at multiple wavelengths, from an incident ending to an output ending, where the guidance path is not necessary straight. Examples are fiber optic, hollow fiber optic, articulated mirror arm. In particular, fibers can be arranged in flexible hoses, thus allowing a transportation of light, especially of high powered laser light, of a long distance, without having the danger that something gets into the laser beam and might be damaged, as this is possible for a free air transmission of a laser beam.

The primary objective of the outlet port is to enable the laser beam leaving the optical light guiding element, to be directed to the target surface and thereby leaving the handheld device. According to a previous embodiment the flexible hose can comprise more supply lines than just an optical light guiding element and therefore it is a further embodiment that the outlet port comprises an outlet opening which is connected to the duct. Therefore the various supply lines arranged within the flexible hose, are provided with a direct outlet at the outlet port of the handheld device and therefore are in the immediate vincinity of the target area.

According to a treatment application it is of advantage, when the light guiding element ending is arranged at least partly around the outlet opening. If for example the outlet opening is connected to a duct providing a pressurized gas with a negative relative pressure, the emitted laser beam ablates material from the target surface which is than sucked into the outlet opening and transported via the duct to a waste compartment in the housing. On the other hand it could be useful if the duct supplies liquid that washes away the material ablated by the laser beam.

An embodiment, where the outlet opening is arranged at least partly around the light guiding element ending, has the advantage that e.g. a controlled atmosphere and environment can be established around the laser beam and thereby removing any free oxygen from the target area. When a high energy light pulse is emitted from the outlet port into free air, ionisations effect can occur, generating unwanted reaction products within the target area. This can be avoided by cloaking the target area with an inert gas.

One objective of the invention is further solved by a treatment device comprising a handheld device with a solid-state laser according to the present invention, a table-top unit comprising an electrical power supply for supplying the handheld device, especially the solid-state laser, with electrical energy and a flexible hose connecting the handheld device with the table-top unit. Due to the inventive use of a low gain laser material, the solid-state laser generates a huge amount of excessive heat when producing a laser beam, which heat has to be removed from the solid-state laser, in order to avoid damaging the laser. Therefore the solid-state laser comprises a cooling unit which, according to the invention, is embodied as cavity. The cooling cavity is connected via two cooling liquid transportation tubes, arranged in the flexible hose, to a cooling liquid circulation system within the table-top unit. This embodiment allows a solid-state laser with a high energy laser beam output, to be arranged in the handheld device and removing the excess heat from the handheld device and transporting it to the table-top unit, where a high efficient cooling system can be arranged. The solid-state laser further comprises a control unit for electrically driving the solid-state laser, which, according to the invention, comprises one high current capacity buffer, providing sufficient electrical current to the pump source for stimulating the laser emission. This current buffer and the heat circulation system provides a laser based treatment device that can provide a high intensity laser beam with a high operation circle, over a long period of time. The contact window has to deliver the laser beam to the target surface, whereby usually a direct contact, or a near arrangement of the contact window with respect to the target surface is possible. After performing the treatment tasks, especially when performing tasks on biological samples, the treatment device and especially the contact window, has to be thoroughly cleaned, especially a disinfection has to be performed. Therefore the contact window has to withstand such chemical treatments and is therefore e.g. embodied as fluor polymers like e.g. MFA, PFA, or FEP.

The objective of the invention is further solved by another embodiment of the treatment device which comprises a handheld device only, wherein the handheld device comprises an energy storage means and where the cooling unit is embodied as solid-state cooling device. For handheld devices it is usually not required to provide a high operation duty circle, nor is a long time continuous operation required. Therefore it is sufficient to have a passive cooling unit attached to the solid-state laser, which takes over the excessive heat and removes it from the laser device, keeping the device within normal operation parameters. As the repetition rate of the treatment operation is less then for a table-top unit based system, the energy storage can be a rechargeable battery like a Li-Ion secondary cell.

The optical pathway is defined by the components guiding the laser beam from the solid-state laser to the contact window, respectively to the target surface. This optical pathway is a crucial part for a proper operation of the treatment device, as any disturbance within the optical path, directly influences the quality of the emitted laser beam. Therefore it is of importance that this optical path is sealed against the surrounding environment, especially that it is sealed against dust and humidity. As the wavelength of the laser beam is preferably tuned to an absorption peek of water ions, any humidity within the optical path causes the laser beam to react on that humidity and therefore heating up the optical pathway and reducing the emitted laser intensity power. By using an encapsulated compartment for the optical path and using O-rings as sealing devices, gaps in the optical pathway can be reduced, or eliminated. The components of the solid-state laser are manufactured to provide a clearance between parts less that 2 µm. The entire optical pathway is tightly sealed to withstand a relative pressure of at least 0.5 bar.

According to a further embodiment, at least two high current capacity buffers and a switching unit are arranged within the handheld device. During operation, the current buffer is charged with electrical energy, over an amount of time, and is discharged over a very short period of time, supplying the pump source for generating the pump light. Having two high current buffers arranged in the handheld device allows one current buffer to be charged, while the other buffer is used for generating the pump light. The switching unit performs the task of connecting the high current buffer either to the pump source or to the charging power supply. This embodiment allows a higher operation rate of the treatment device.

For easing the configuration and operation of the treatment device it is further of advantage, when the handheld device comprises a user interface, which comprises a display unit and an input device. Therefore the user of the handheld device has an individual configuration and operation control possibility arranged directly on the handheld device and has therefore the ability to control the treatment without interrupting the treatment procedure as all process information and control possibilities are available on the handheld device.

As the treatment area is usually quiet narrow and therefore a direct view is often not possible, it is of advantage, when the handheld device comprises an image acquisition and analysis unit. This allows an image to be gathered, processed and provided to the user, e.g. by a display means, who than has a much better view of the target area, respectively where the laser beam hits the target surface. In a further embodiment a stereographic image could be gathered, providing a 3D image to the user.

A handheld device which is detachable from the table-top unit has the advantage that e.g. individual handheld devices with solid-state lasers operating on different wavelengths can be connected with the table-top unit for building the treatment device. This embodiment has the further advantage that the exchange, respectively the maintenance of the solid-state laser or other components within the handheld device, is much more simplified, as the handheld device may be detached from the table-top unit, respectively from the flexible hose, and a new or other handheld device is attached to the table-top unit, respectively to the flexible hose. During the intended usage it may be possible, that the solid-state laser, respectively the laser gain medium or the laser diode, may become damaged or their operation parameters deteriorate. Due to the robust construction of the solid-state laser it is possible to detach the handheld device with the solid-state laser from the table-top unit, or from the flexible hose, and ship it to a service and maintenance unit, without taking special care that the solid-state laser withstands the rough treatment on a standard shipment procedure. The user can have two handheld devices available at the treatment location, one in use and the other as exchange part, when the first device has to be sent to maintenance. With previous laser systems the maintenance was a quiet difficult task, as it usually required an interruption in the usage and a technician on site, who has to perform the maintenance tasks.

According to another advantageous embodiment, the transparent covering is detachable from the handheld device, thus allowing the part that gets in direct contact with the material to be treated to be removed from the device and e.g. discarded or thoroughly cleaned. When ablating material it may be possible that the covering gets contaminated with the ablated material, and has to be thoroughly cleaned before next use. This is especially important when treating human tissue, where a material spread must be avoided. A detachable covering therefore reduces the need to perform an intensive cleaning of the entire handheld device, especially a single-use cover can be used.

When dissipating the excess heat from the solid-state laser by the solid-state cooling unit, a free flow air cooling is not suitable, as it is not capable of removing the excess heat in the available amount of time. Therefore a phase state change material like paraffins, fluorides, carbonates, chlorides, hydroxides, nitrates, salt nitrates, sugar alcoholes, fatty acids, chlatrates, metals (e.g. gallium), metal alloys, combinations of the aforementioned materials with heat conduction increasing materials (e.g. graphites, polymeres, metals, semiconductors, ceramics, crystalline materials, diamond-copper, silicon carbide, graphitic carbon), is used, as changing the state of the material, e.g. from solid to liquid or from liquid to gaseous, can absorb a huge amount of thermal energy and dissipate the stored energy via a longer period of time to the ambient. Most preferably is a material that has a reversible phase state change, as this allows a usage multiple times.

BRIEF DESCRIPTION OF THE DRAWINGS

The present invention can be better understood and its advantages appreciated by those skilled in the art by referencing to the accompanying drawings. Although the drawings illustrate certain details of certain embodiments, the invention disclosed herein is not limited to only the embodiments so illustrated.

FIG. 26 a) to d) depicts embodiments of a working tip.

DETAILED DESCRIPTION

Figure 1:
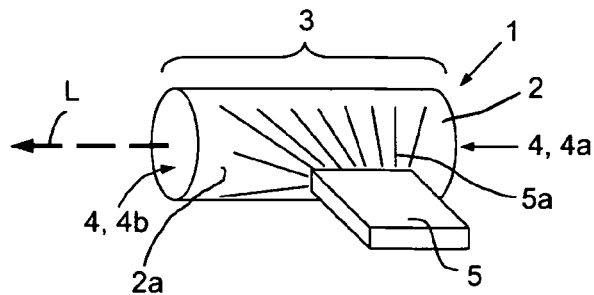
FIG. 1 depicts a diagram of a monolithic, side-pumped solid-state laser.

Reference will now be made in detail to particular embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale.

In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

As used herein the term conductive cooler or cooler means including but not limited to a heat energy transport medium (e.g. liquids, gases, solid materials), a heat spreader (e.g. metals such as copper, gold, aluminum or many more or alloys thereof; ceramics such as Beryllium oxide, Aluminum nitride, Aluminum oxide, Zirconium oxide or many more; crystalline materials such as diamond, sapphire, silicon carbide) or a heat energy storing buffer element. A liquid heat energy transport medium may in particular be a circulating, moving or still standing liquid that is at least partially transparent for the pump light. The liquid heat energy transport medium may for example be water, water-glycol mixtures, ethanol or other heat transfer fluids like e.g. the Solvay Solexis Galden™ HT200. Galden™ is a trademark of Solvay Solexis Inc. Another type of conductive cooler could be a thermally conducting liquid like liquid metals and liquid metal alloys, for example gallium or liquid metal alloy or mixtures or for example a liquid metal alloy called Galinstan® that can be purchased from Geratherm, Germany and which is less corrosive than pure gallium. Yet another type of conductive cooler could be a thermally conducting foil made of graphite, indium or other metals, which could be even used to solder the crystals to the cooler.

As used herein the term reflector means including but not limited to surfaces that fully or partially or diffuse reflect or back scatter light. A full reflecting surface can be a polished metal surface coated with e.g. gold, silver, aluminium, platinum or even a dielectric coating. Another full reflecting surface could be made of a crystalline material that is coated with a dielectric coating like an optical laser mirror. A partially reflective or diffuse reflector can be a rough surface or a partially pump light transparent material that can diffuse and reflect light such as e.g. a sand blasted gold coated metal surface that scatters the light back more than directly reflects the light back. Another type of reflector could be a ceramic material that partially absorbs the light but reflects most of the light in a scattered way than in a reflective way. Another type of reflector can be made of a kind of plastic material that is called Spectralon®. Another type of reflector could be a thermally conducting liquid like liquid metals and liquid metal alloys, for example gallium or a liquid metal alloy called Galinstan® that can be purchased from Geratherm, Germany and which is less corrosive than pure gallium. Yet another type of reflector could be a reflective foil made of indium or other metals, which could be even used to solder the crystals to the cooler.

As used herein the term mirror or laser mirror means including but not limited to surfaces or substrates the fully or partially reflect light. Such a substrate can be a polished piece of metal or crystalline material (e.g. YAG, sapphire, fused silica, . . . ) where the at least partially reflecting surface is established with a metal coating (e.g. of gold, silver, aluminium, platinum) or a dielectric coating.

Another laser mirror with an at least partially reflecting surface could be made of a substrate from crystalline material that is coated with a dielectric coating. The substrate can then be diffusion bonded onto the laser crystal, which is kind of an atomic level, usually not separable component bonding or joining technique.

Since usually a high reflecting mirrors cannot be reflect light 100%, there is always a laser output also on this side of the laser. The smaller the reflecxtivity, the higher the laser power on the high reflecting side is. A special combination of laser and partial and high reflector can lead to a laser system which has almost the same output power on both sides.

The laser mirror can also be made of a metallic or dielectric coating directly onto a laser active material. This laser mirror at least partially reflects the desired emission wavelength of the laser active material. A laser mirror is called high reflector (FIR) if the reflectivity is about 99% and above. A laser mirror is called output coupler (OC) if the reflectivity is below 99% or the other way around, more than 1% of the laser light leaves the cavity. Optical coatings, in particular dielectric coatings are deposited in multiple layers by PVD (physical vapour deposition) or CVD (chemical vapour deposition) techniques. In particular PVD is widely used for optical coating layers whereas the technologies differ between EBS or EBC (electron beam sputtering or electron beam coating), magnetron sputtering, IBS (ion beam sputtering), IAP (ion assisted plating), IP or RLVIP (Ion plating or Reactive Low Voltage Ion Plating), MBE (molecular beam epitaxy), MOCVD (metal organic chemical vapor deposition), MOVPE (metal organic chemical vapor phase epitaxy), and many others. The coatings shall not contain materials (like e.g. OH-bonds) that well absorb laser light with wavelengths between 1700 and 3200 nm. Another cause of damage to a mirror is the absorption of laser light in the layers of such a mirror. Therefore it is advantageous to use low absorbing layer materials in the desired wavelength range like $TiO_2$, $Ta_2O_2$, $HfO_2$, $Nb_2O_5$, $Al_2O_3$, $SiO_2$. For specific application it is advantageous to use coatings consisting of metal and/or metal oxide combinations like e.g. Si and $SiO_2$, thorium fluoride and zink selenide or combinations of several different materials in one coating. For example a very low absorbing material combination can be used for the parts of a mirror with the highest optical power, but sometimes these materials are limited in the number of layers respectively reflectivity. In order to further increase the reflectivity, a material combination, which can be grown to high number of layers respectively reflectivity, but with a slight absorption can be added on top where the optical power is already decreased. Such a combination of materials allow to produce e.g. mirrors with very high damage thresholds and very high reflectivities. Preferably such a layer material has an absorption of less than 2% per layer, in particular less than 0.5% per layer, and, most preferably less than 0.1% per layer. The coatings shall therefore not be made of materials that well absorb laser light with wavelengths between 1700 and 3200 nm. The main difference between the coating processes is the deposition energy. If the deposited materials have a low energy at least one coating layer can contain microvoids or pores. The voids create lower packing density (the ratio of the volume of the solids in the layer to the layer's total volume) that results in less dense layers. Typical layer packing densities for less dense layers are in the range of 0.75 to less than 0.9. Less dense layers are less stable environmentally and when the layer is exposed to humidity, the microvoids eventually fill up with water. Laser wavelengths in the mid infrared are strongly absorbed by water and therefore the water in the microvoids can vaporize and damage the layer, respectively the laser mirror. Therefore only laser mirrors consisting of layers with a packing density of greater than 0.90 or even greater than 0.99 should preferably be used in laser systems in the MIR (mid infrared). Such high density layers may be achieved using IBS (ion beam sputtering), IAP (ion assisted plating) techniques to deposit the coating layers. In a most preferred embodiment the deposited materials have a very high energy leading to packing densities greater than 1.05 or 1.10. Such very high density layers which are also called overdense layers may be achieved using IP (Ion plating), RLVIP (Reactive Low Voltage Ion Plating) or MBE (molecular beam epitaxy) techniques to deposit the coating layers.

As used herein dense layer refers to a layer with a packing density of greater than 0.9, preferably greater than 0.95 and more preferably greater than 0.99. Most preferably dense layers have a packing density of greater than 1.05 or 1.1.

As used herein semiconductor laser or diode lasers or laser diodes refers to, including but not limited to, laser diodes, laser diode arrays, VCSELs (vertical cavity surface emitting laser), VECSELs (vertical external cavity surface emitting laser), lead salt lasers, quantum dot lasers, quantum well lasers, quantum cascade lasers, semiconductor ring lasers, hybrid silicon lasers. As used herein the term "low gain material" or "low gain laser active material" refers to gain materials/laser active materials/laser active media/laser gain media with a stimulated emission cross section equal or less than that of Er:YAG namely $<=3.0*10^{-20}$ $cm^2$. Examples are, including but not limited to:

Er:YAG (Erbium doped YAG laser crystal host) . . . 2, $6\sim3.0*10\text{-}20$ $cm^2$ Er:YSGG (Erbium doped YSGG laser crystal host) . . . $6.5*10^{-21}$ $cm^2$ Er:YLF (Erbium doped YLF laser crystal host) . . . $12.5*10^{-21}$ $cm^2$ Cr,Er:YSGG (Chromium-Erbium doped YSGG) . . . $5.2*10^{-21}$ $cm^2$ Ho:YAG (Holmium doped YAG laser crystal host) . . . $1.2*10^{-20}$ $cm^2$ Ho:YLF (Holmium doped YLF laser crystal host) . . . $1.47*10^{-20}$ $cm^2$ CTH:YAG or Cr:Tm:Ho:YAG (Chromium-Thulium-Holmium doped YAG laser crystal host) . . . $7*10^{-21}$ $cm^2$ Ho:Tm:Er:YLF (Holmium-Thulium-Erbium doped YLF laser crystal host) . . . $1.8*10^{-21}$ $cm^2$ Tm:YAG (Thulium doped YAG laser crystal host) . . . $1.5\sim2.5*10^{-21}$ $cm^2$ Tm:YAP (Thulium doped YAP laser crystal host) . . . $5.0\sim6.0*10^{-21}$ $cm^2$ Ho:Tm:YAG (Holmium-Thulium doped YAG laser crystal host) . . . $9*10^{-21}$ $cm^2$ Tm:Ho:YLF (Holmium-Thulium doped YLF laser crystal host) . . . $5*10^{-21}$ $cm^2$ Relevant laser crystal host materials are e.g.

YAG (yttrium aluminium garnet)
YSAG (yttrium scandium aluminium garnet)
YSGG (yttrium scandium gallium garnet)
YGG (yttrium gallium garnet)
GdVO (Gadolinium Vanadate)
GGG (gadolinium gallium garnet)
GSAG (gadolinium scandium aluminium garnet)
GSGG (gadolinium scandium gallium garnet)
LLGG (lanthanum lutetium gallium garnet)
YAP (yttrium aluminium perovskite)
YLF (yttrium lithium fluoride)
BYF (Barium Yttrium Fluoride)
Ceramic host crystals like YAG, $Lu_2O_3$, $Sc_2O_3$ and $Y_2O_3$ FIG. 1 illustrates a monolithic, side pumped solid-state laser 1 as used with an embodiment of this invention. The basic laser architecture is intentionally made simple. The laser 1 includes a laser gain medium 2, preferably an Er:YAG. The laser resonator 3 is formed by the end faces 4 of the monolithic block structure, with a high reflector (HR) laser mirror 4a deposited directly on the gain medium 2 and an output coupler (OC) laser mirror 4b deposited directly on the opposite end on the gain medium 2. The output coupler 4b has most preferably a reflectivity in the range of between 92.5% and 99%, which means that about 1% to 7.5% of the laser light is leaving the gain medium 2 through the output coupler 4b. The gain medium 2 is side pumped on a pump face 2a by a pump source 5. The pump source 5 comprises a least one semiconductor laser, preferably a diode laser array emitting a light beam 5a. The laser resonator 3 having a diameter of less or equal 3 mm, and therefore having a cross section area of about less than 7.5 $mm^2$.

The side pumped solid-state laser 1 disclosed in FIG. 1 is a plano-plano resonator, also called flat-flat resonator which means that the end faces are orthogonal to the optical axis L with an angle deviation of equal or less than 0.05° with respect to 90° to the optical axis L, comprising a high reflectivity laser mirror 4a and an outcoupling, partially transmitting laser mirror 4b, the outcoupling laser mirror 4b having a transmission of between 1% and 7.5%. For certain applications intracavity elements 11, such as an electro-optic or acousto-optic cell for Q-switching, or an etalon for wavelength tuning can be introduced between the laser rod and the laser mirror. A saturable absorber or a bleachable absorber or SESAM might be suitable for Q-switching also. The saturable absorber can act as a transmissive or a reflective element. The saturable absorber could be made of one of the herein mentioned host materials and can be doped for example with rare earth elements. The saturable absorber could also be diffusion bonded directly onto the laser active gain material. The laser 1 can emit energy in, for example, one of the following modes of operation: CW, gain switched obtained by quasi-CW operation of the pump diode laser, or pulsed modus which means pump modulation. FIG. 1 discloses a gain medium 2 with plane end faces 4 covered by a plane reflectivity laser mirror 4a and an outcoupling laser mirror 4b. In a further advantageous embodiment at least one end face 4 may have a convex, a concave, an aspherical convex or an aspherical concave shape or even a flat surface with an angle, so called wedge, between 89.7°-90.3° with respect to the optical axis L (laser output axis) to compensate very little asymmetry or thermal lensing problems, so that the reflectivity laser mirror 4a and the outcoupling laser mirror 4b deposited directly on the end face 4 adopt the shape of the respective end face 4. Such laser mirrors 4a, 4b on both ends of the laser resonator 3 allow a beam shaping or allow adjustment of a thermal lens. Due to very short laser cavities a use of a convex or concave end face requires high precision in laser gain material manufacturing. One of the important properties with such curved end faces is the need of a centricity of equal or less than 3 minutes of angle with respect to the optical axis L. The laser gain medium 2 consists most preferably of a low gain laser active material.

The solid-state laser 1 disclosed in FIG. 1 can also comprise a q-switch that is positioned outside of the cavity. It could be positioned on the output coupler an act as an additional reflecting surface to increase the intracavity laser power until the q-switch switches due to bleaching (e.g. a saturable absorber or SESAM) or is activated/deactivated actively via control means and the reflectivity is turned from full reflection of the outcoupled light back into the laser into full transmission of the outcoupled light.

The solid-state laser 1 disclosed in FIG. 1 also comprises a cooling, which is not shown in detail. Examples of cooling arrangements are for example disclosed in FIGS. 2 to 7.

The embodiment disclosed in FIG. 1 has the advantage that the small diameter of the circular laser gain medium of less or equal 3 mm, respectively of the cross section area of about less than 7.5 mm$^2$ allows a more or less homogenous high intensity of the pump light 5a of the pump source 5 within the laser gain medium 2, so that a homogenous high intensity of laser light is generated within the laser gain medium 2. In addition the relatively high reflectivity of the output coupler 4a in the range of between 92.5% and 99% allows efficient generation of an output laser beam B of high intensity. In addition providing both end faces 4 with a reflective coating 4a, 4b reduces the loss of laser light at the end faces 4, which also contributes to a laser beam B of high intensity. All measures in combination allow building a diode side pumped solid-state laser being able to emit a high quality laser beam, which can be focused to an intensity in the range of about 1 W/mm$^2$ and 10$^8$ W/mm$^2$. The solid-state laser 1 according to the invention therefore shows high efficiency, so that moderate pump power of the pump source 5 is sufficient to create a laser beam B with desired power and quality. In FIG. 1 the cross section of the laser gain medium 2 is of circular shape. The cross section of the laser gain medium 2 may have other shapes, such as rectangular, triangle, polygonal or square.

Figure 1A:
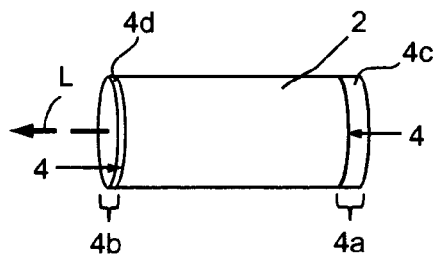
FIG. 1a,1b,1c depicts embodiments of the end faces of the laser gain medium.

FIG. 1a illustrates the laser gain medium 2 in detail, and shows the end face 4 on the right side covered by a polished metal block or surface 4c bonded onto the end face 4 and thereby forming the high reflecting (HR) laser mirror 4a. The left end face 4 is coated by a substrate 4d such as a metallic layer or a semiconductor layer, thereby forming an output coupler (OC) laser mirror 4b.

Figure 1B:
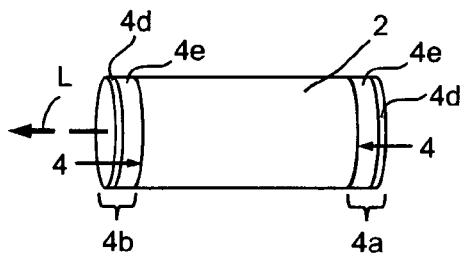

FIG. 1b shows another embodiment of a laser gain medium 2 in detail with laser mirrors 4a and 4b, the laser mirrors 4a and 4b comprising a crystalline structure 4e coated by a substrate 4d such as a metallic layer or a semiconductor layer. The crystalline structure 4e is bonded onto the end faces 4. The crystalline structure 4e can act as stress reducing elements to improve lasing stability and decrease thermal lensing effects which contributes to high laser stability over a wide working range. The crystalline structure 4e can also contribute to more stable optical coatings than optical coatings which are deposited directly onto the crystal and then often get damaged through thermal overload.

Figure 1C:
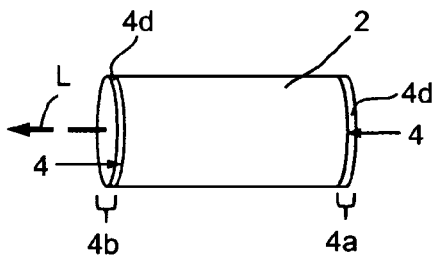

FIG. 1c shows another embodiment of an laser gain medium 2 in detail with laser mirrors 4a and 4b consisting of a substrate 4d such as a metallic layer or a semiconductor layer coated onto the end faces 4. Such laser mirrors 4a and 4b are attached to the end face 4 of the laser gain medium 2, thereby forming a high reflecting laser mirror 4b respectively a laser mirror 4a to at least partially reflect the laser light B.

Figure 1D:
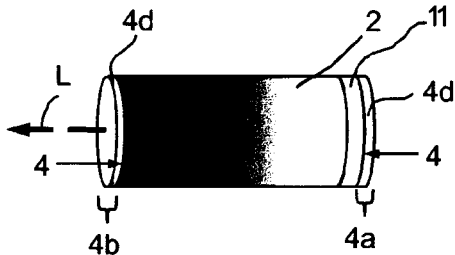
FIG. 1d, 1e depicts embodiments of laser cavities including a q-switch.
Figure 1E:
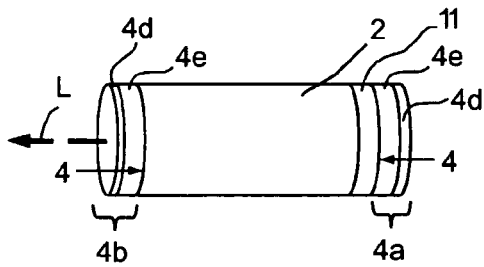

FIG. 1d shows an embodiment including a q-switch or a saturable absorber 11. FIG. 1e shows a further embodiment including a q-switch or a saturable absorber 11. In the embodiments according to FIGS. 1d and 1e, the q-switch 11 could also be arranged between the laser active medium 2 and the output coupler (OC). Combinations of the embodiments disclosed in FIGS. 1 to 1e are of course also possible.

Figure 2:
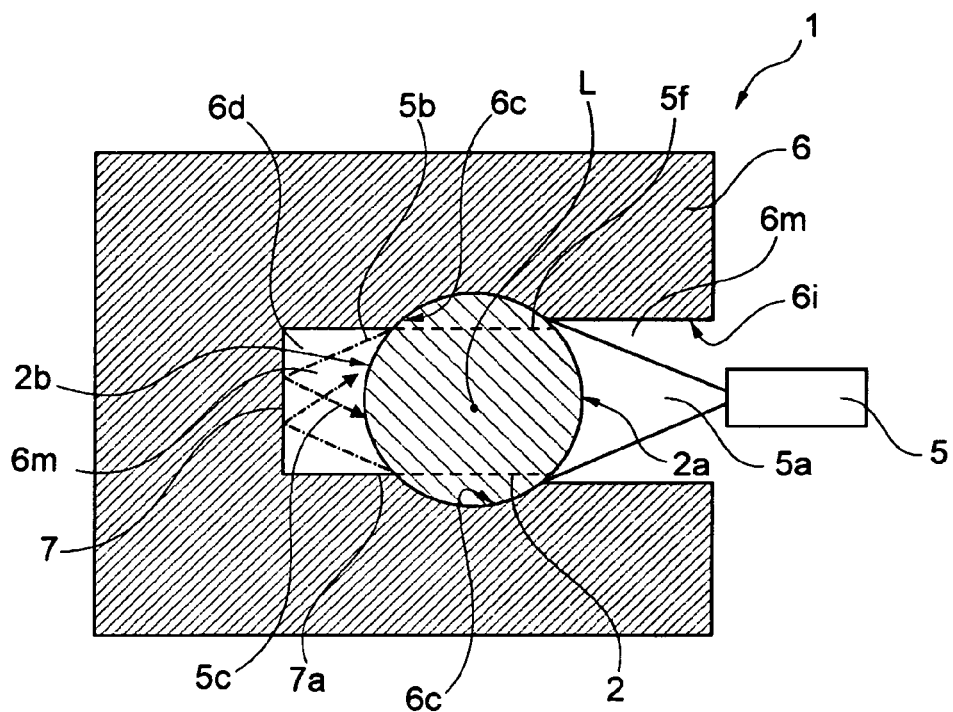
FIG. 2 depicts a symmetrically cooled solid-state laser with direct pump light incoupling.

FIG. 2 illustrates an advantageous embodiment of a monolithic, side pumped solid-state laser 1 comprising a laser crystal or gain medium 2 thermal conductively connected with a conductive cooler 6. The conductive cooler 6 is also holding the gain medium 2. A pump source 5 is arranged on the side of the gain medium 2. A reflector 7 is arranged at the opposite side of the pump source 5. In addition to the reflector 7 also the conductive cooler faces 6c might comprise reflective characteristics, for example by an appropriate coating, so that the cooler faces 6c could be used as reflectors also. The pump light 5a of the pump source 5 enters the gain medium 2 at a side face 2a and leaves the gain medium 2 at an opposite side face 2b. Depending on the absorption of the laser beam 5a in the gain medium 2, an exit beam 5b, which means the fraction of the laser beam 5a not being absorbed within the gain medium 2, exits the gain medium 2, whereby the not absorbed/remaining pump light 5b hits the reflector 7 and is at least partially reflected causing a reflected laser beam 5c, which enters the gain medium 2. Depending on optical properties of the gain medium 2 and the pump source 5 which is a diode laser, the laser beam 5f might traverse the gain medium 2 in parallel direction or also in another direction. FIG. 2 discloses a direct pump light incoupling of the laser beam 5a into the laser crystal 2. The pump light emitted by the diode laser 5 is guided trough a slit 6e to the crystal 2. The slit 6e could also be filled with a pump light transparent material like e.g. YAG (yttrium aluminum garnet) or sapphire and thus facilitate more homogeneous and symmetric thermal heat transport which finally stabilizes the solid-state laser additionally. Additionally the transparent material could be designed as a waveguide for the pump light to further improve the pump light distribution inside the laser crystal. This embodiment discloses a symmetrically cooled solid-state laser gain medium 2 in that the laser crystal 2 is symmetrically arranged and held in the cooler 6. In the most preferred embodiment the monolithic, side pumped solid-state laser 1 comprising a laser resonator composite structure 3 comprised of a laser gain medium 2 having a longitudinal axis L, wherein the laser comprising a conductive cooler 6 comprising contact faces 6c contacting the laser gain medium 2, whereby the contact faces 6c are most preferably symmetrically arranged with respect to the longitudinal axis L of the laser gain medium 2. Most preferred this embodiment allows cooling the laser gain medium 2 such that there is a symmetric cooling with respect to the longitudinal axis L. One purpose of the conductive cooler 6 is to transport the heat from the laser gain medium 2 to a heat sink which is not shown. The heat sink might for example be the outer surface of the conductive cooler 6. The conductive cooler 6 may also be connected with an additional cooler such as a thermo electric cooler and/or a forced air cooled heat sink, or a thermo electric cooler and/or a water cooling system not shown in FIG. 2. The conductive cooler 6 consists of a material suitable for transporting heat, most preferably the conductive cooler 6 is made of metal such as copper or ceramics or of a crystalline material or another material herein referred to as suitable for a reflector. As disclosed in FIG. 2 the conductive cooler 6 comprises a cooler cavity 6d arranged beside the laser gain medium 2 and arrange opposite to a side face 2a. The pump light 5a entering the laser gain medium 2 through the side face 2a. The reflector 7 is arranged in the cooler cavity 6d, which also means that the reflector 7 may be a reflecting surface of at least one side wall of the cooler cavity 6d, whereby the side wall may also be coated with a reflective coating. Further measures may be taken to improve the heat transfer from the gain medium 2 to the conductive cooler 6 by applying a thermal compound between the gain medium 2 and the conductive cooler 6, such as a thermal heat sink paste, or a liquid metal such as gallium, or a mixture of a liquid metal comprising one or more particles of a solid metal.

The symmetric heat transfer is essential for a monolithic laser resonator structure 3 operating over a wide range of pump light 5a power. A laser crystal 2 with the space 6d replaced by the contact face 6c gets unstable with high pump light 5a powers and the laser resonator structure 3 stops to generate laser radiation. The symmetric heat transfer in the embodiment illustrated in FIG. 2 results in a symmetric thermal lens, which does not destabilize the laser resonator structure 3 and allows generating laser radiation over a wide range of pump light 5a powers. It is also possible to compensate an asymmetric heat transfer, respectively thermal lens, by angled end faces 4, but this limits the efficient operation of the laser resonator structure to just one specific pump light 5a power.

Figure 2A:
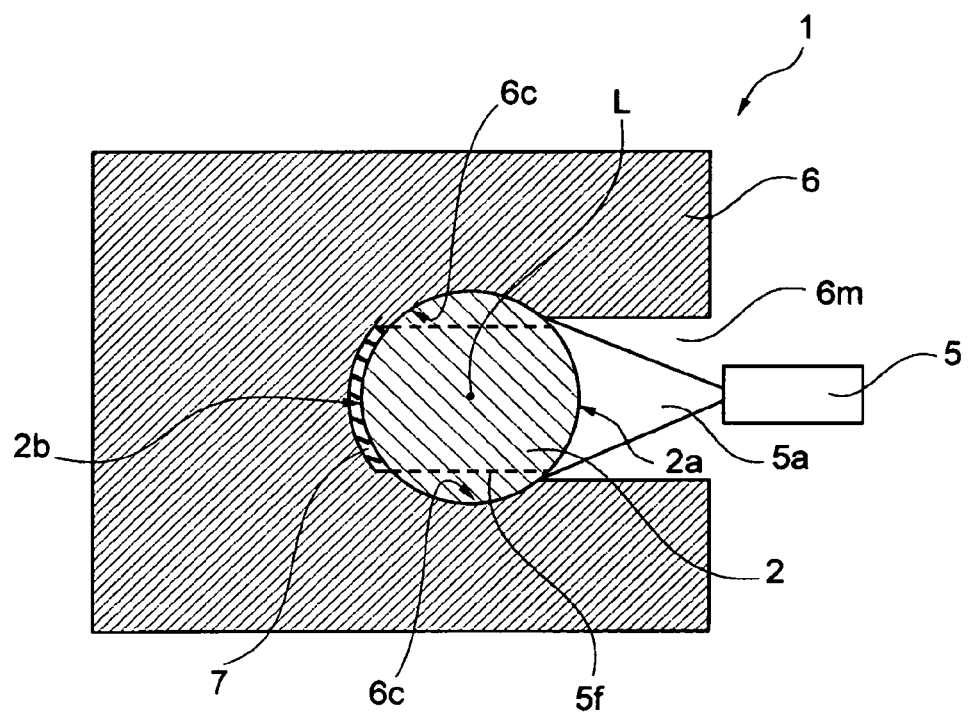
FIG. 2a depicts another symmetrically cooled solid-state laser with direct pump light incoupling.

FIG. 2a illustrates another advantageous embodiment of a monolithic, side pumped solid-state laser 1 comprising a laser crystal or gain medium 2 thermal conductively connected with a conductive cooler 6. Laser 1 comprising a reflector 7 arranged opposite to the side face 2a with respect to the longitudinal axis L and the reflector 7 being arranged just beside the laser gain medium 2 or the reflector 7 being arranged just on the laser gain medium 2.

Figure 3:
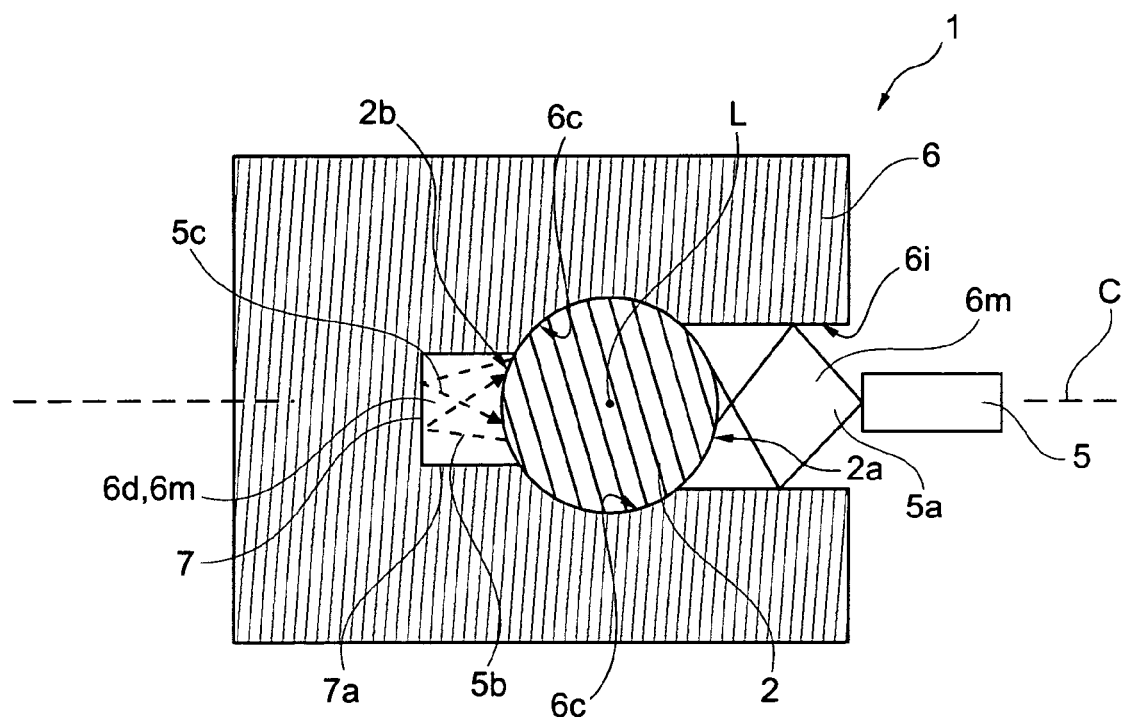
FIG. 3 depicts a symmetrically cooled solid-state laser with indirect pump light incoupling.

FIG. 3 illustrates a further embodiment of a monolithic, side pumped solid-state laser 1 comprising a laser crystal or gain medium 2 thermal conductively connected with the conductive cooler 6. A pump source 5 is arranged on the side of the gain medium 2. In contrast to the embodiment according to FIG. 2, the embodiment according to FIG. 3 discloses an indirect pump light incoupling of the laser beam 5a into the laser crystal 2, in that, as disclosed in FIG. 3, at least part of the laser beam 5a is reflected on the inner surface 6i of the cooler 6 before entering the gain medium 2. The inner surface 6i is the surface of the gap of the cooler 6 leading from the diode laser 5 to the laser gain medium 2. The advantage of the longer pathway for the pump light 5 is a better mixing/diffusing of the pump light 5 and a more homogeneous pumping of the gain medium, the crystal 2. The pathway is also of advantage for using different diode lasers 5 having different emission angles which means one can use diode lasers with high or with low brightness. The exemplary embodiment disclosed in FIG. 3 is symmetric with respect to plain C. The width of the inner gap 6m of the cooler 6 may for example vary, as disclosed in FIG. 3 or may for example have the same width, as disclosed in FIG. 2.

Thermal management and temperature control of the conductive cooler 6 are most advantageously provided by air cooling with the possibility of also using thermo-electric cooling but also water cooling might be suitable.

Figure 4:
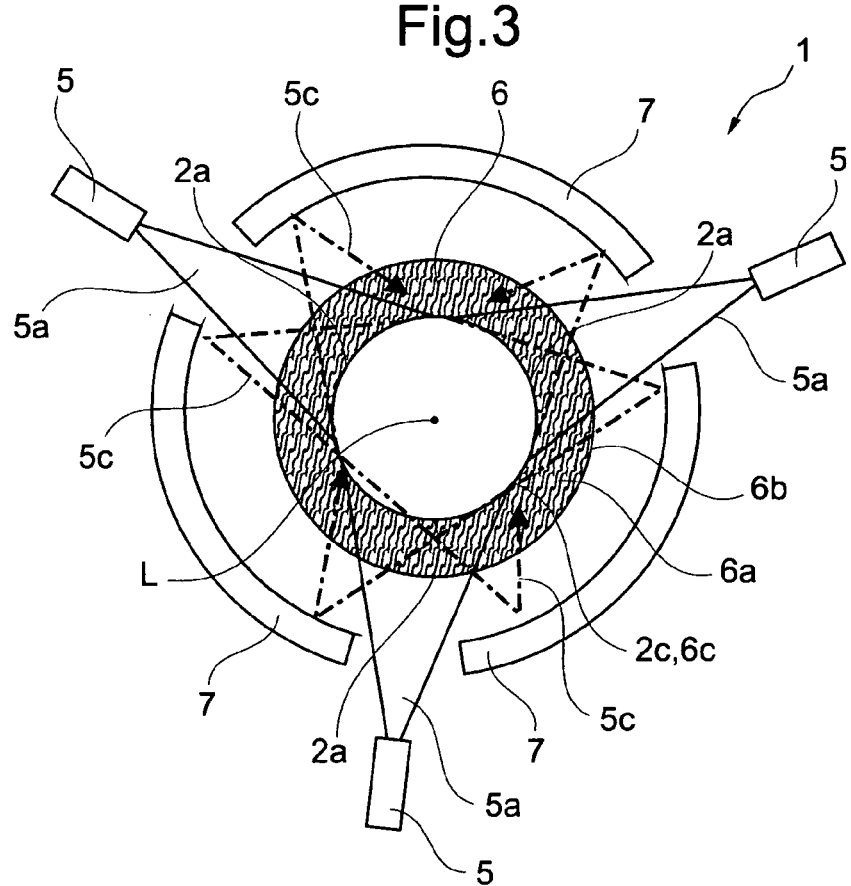
FIG. 4 depicts a radial symmetrically and liquid cooled laser.

FIG. 4 illustrates a further embodiment of a monolithic, side pumped solid-state laser 1 comprising a laser crystal or gain medium 2 thermal conductively connected with a cooler 6. The gain medium 2 is in longitudinal direction L surrounded by a fluid, in particular water or water containing cooling fluid which is flowing in between the outer crystal surface 2c and a tubular member 6b of the cooler 6, the tubular member 6b being concentrically arranged with respect to the longitudinal axis L. In the example disclosed three pump sources 5 are spaced apart by 120° with respect to the longitudinal axis L of the gain medium 2, and are arranged along the side of the gain medium 2. Three corresponding reflectors 7, each arranged at the opposite side of the respective pump source 5, are arranged such that the pump light 5a of the pump source 5 enters the gain medium 2, and an exiting, not absorbed/remaining pump light 5b, which is the portion of the pump light 5a leaving the gain medium 2 opposite to the side face 2a, exits the gain medium 2, whereby the exiting pump light 5b hits the reflector 7 and is at least partially reflected by the reflector 7, forming a reflected exit pump light 5c, a least part of which enters the gain medium 2 again. FIG. 4 discloses a direct pump light incoupling of the pump light 5a into the laser active medium 2. This embodiment discloses a symmetrically cooled gain medium 2 in that the laser crystal 2 is symmetrically arranged and held in the cooler 6, which comprises a tubular member 6b concentrically arranged with respect to the laser active medium 2, the outer tubular member 6b and the surface 2c of the laser crystal 2 delimiting a volume the fluid cooling medium can flow through. The cooler 6 could also be built as a solid, hollow tubular member surrounding the gain medium 2 and preferably being in direct contact with the gain medium 2. Such a solid cooler 6 can for example be built of metal such a copper. The embodiment disclosed is symmetrically with respect to the longitudinal axis L, whereby the elements reflector 7 and pump source 5 are arranged at a respective angle of 120°, but any other symmetrical angle distribution of the arrangement may be useful.

Figure 5:
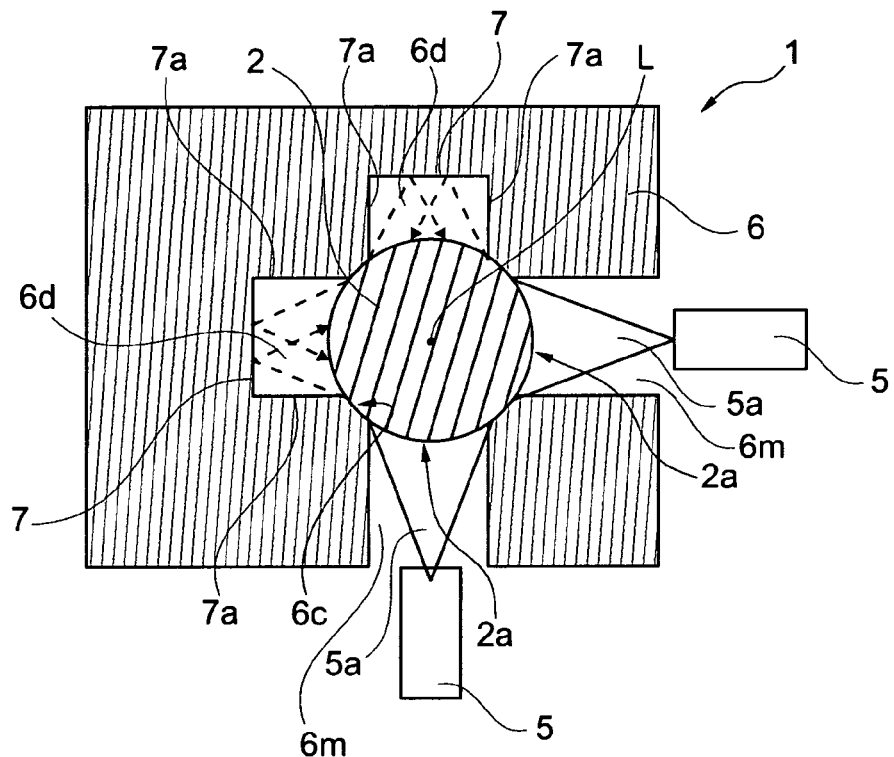
FIG. 5 depicts a symmetrically cooled solid-state laser with direct pump light incoupling comprising two pump lights.

FIG. 5 illustrates a laser 1 of similar design than the embodiment shown in FIG. 2 but comprising two diode lasers 5 spaces apart by 90° with respect to the longitudinal axis L. The laser 1 comprising a conductive cooler 6 comprising contact faces 6c contacting the laser gain medium 2, whereby the contact faces 6c are symmetrically arranged with respect to the longitudinal axis L of the laser gain medium 2. The contact faces 6c could also be used as reflectors, as well as the walls 7, 7a of the cooler cavity 6d, in particular the side walls 7a.

Figure 6:
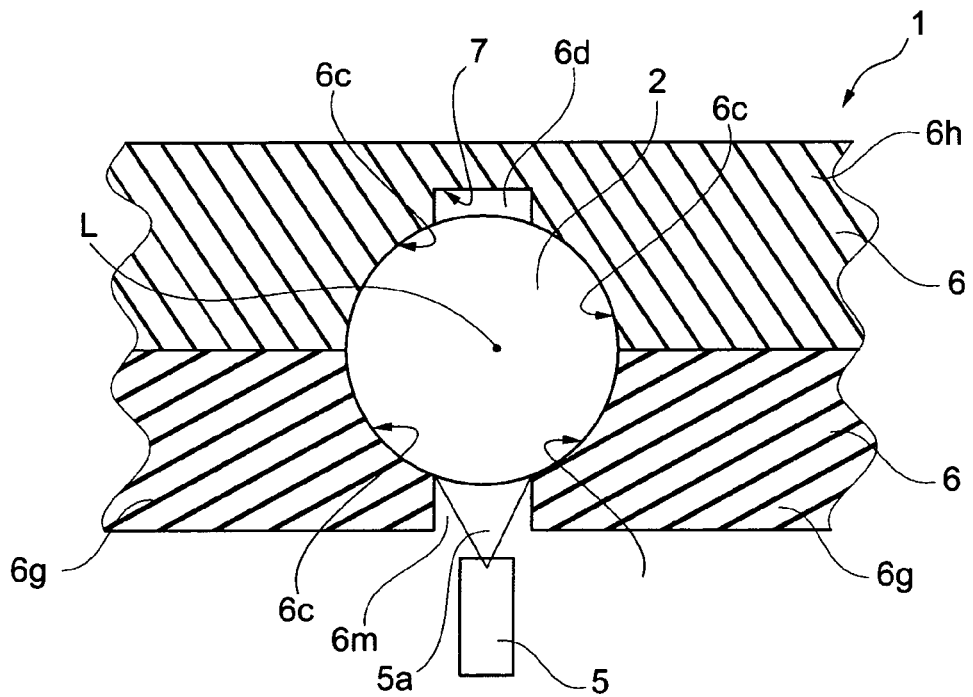
FIG. 6 depicts a cross-sectional view of an example of an arrangement of the laser rod in a heat-sink.

FIG. 6 illustrates another laser 1 of similar design than the embodiment shown in FIG. 2. The laser 1 comprising a conductive cooler 6 comprising contact faces 6c contacting the laser gain medium 2, whereby the contact faces 6c are symmetrically arranged with respect to the longitudinal axis L of the laser gain medium 2. The conductive cooler 6 comprising an upper part 6h and two lower parts 6g, whereby the laser gain medium 2 is clamped between the upper part 6h and the two lower parts 6g. The conductive cooler 6 comprises a slit 6e allowing the light of the diode laser 5 to enter the laser gain medium 2. Opposite to the slit 6e the conductive cooler 6 comprises a cooler cavity 6d so that the contact faces 6c are symmetrically arranged with respect to the longitudinal axis L of the laser gain medium 2. The cooler cavity 6d comprises a reflector 7 to reflect the light exiting the laser gain medium 2. Also the side walls 7a of the cooler cavity 6d could be used as a reflector.

Figure 7:
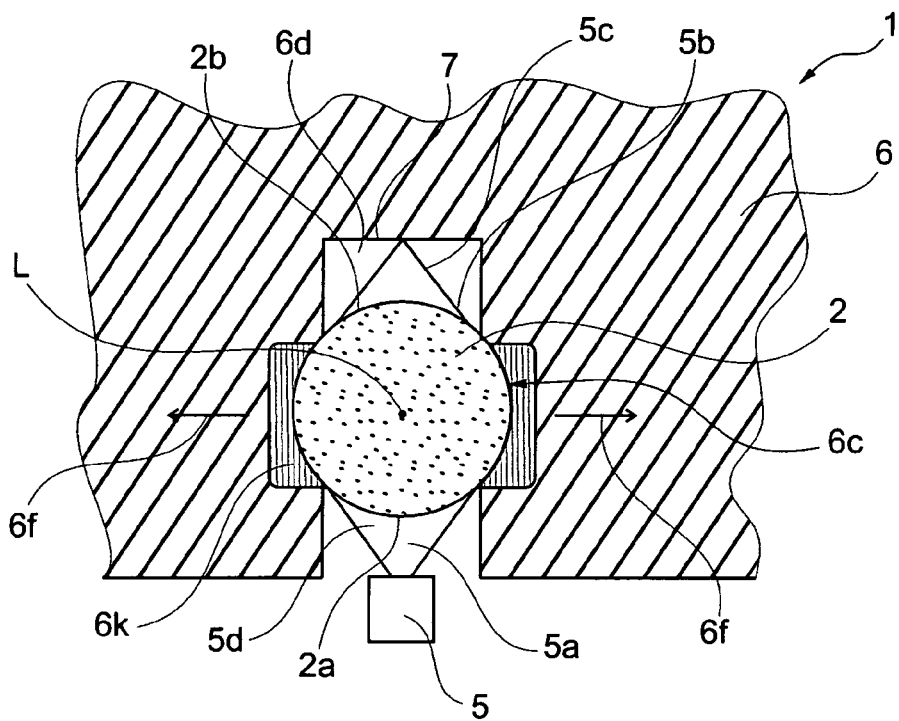
FIG. 7 depicts a cross-sectional view of a further example of an arrangement of the laser rod in a heat-sink.

FIG. 7 illustrates another laser 1 of similar design than the embodiment shown in FIG. 2. The laser 1 comprising a thermally conductive cooler 6, for example a metallic cooler 6, and a heat conductive substance 6k thermally connecting the laser gain medium 2 with the cooler 6, so that a heat flow 6f occurs between the laser gain medium 2 and the cooler 6 when light of the diode laser 5 is emitted into the laser gain medium 2 and heating the laser gain medium 2. The contact faces 6c of the gain medium 2 with the heat conductive substance 6k are symmetrically arranged with respect to the longitudinal axis L of the laser gain medium 2.

Figure 10:
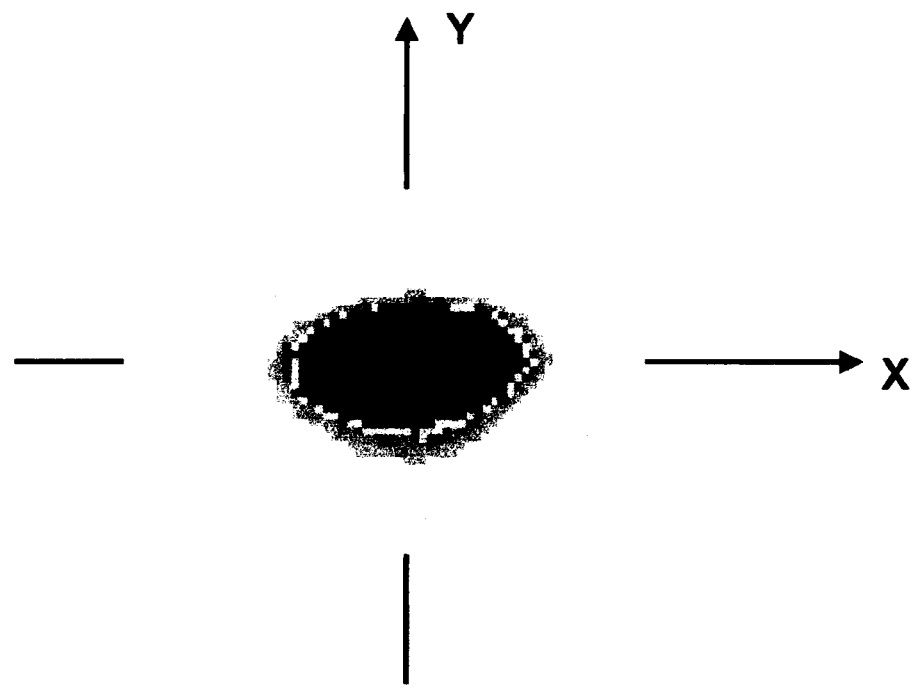
FIG. 10 depicts the energy density of the emitted laser beam.

FIG. 10 shows schematically the energy distribution respectively the signal intensity in x- and y-direction of a laser beam B emitted by the laser gain medium 2 of the laser 1 disclosed in FIG. 7. The symmetrical heat flow 6f causes the elliptical energy density. One advantage of the embodiment according to the invention is that most preferably there is a symmetrical temperature distribution in the laser gain medium 2, similar to the energy distribution disclosed in FIG. 10. Most preferably the temperature distribution stays symmetrically or about symmetrically in a wide range of power inputted by the diode laser 5 into the laser gain medium 2. This effect is achieved by cooling the laser gain medium 2 symmetrically with respect to the longitudinal axis L. This arrangement allows reducing thermal aberrations during operation of the laser. The symmetric cooling geometry according to the invention avoids uncompensated thermal gradients which normally result in lensing, stress induced birefringence and other optical aberrations. The laser 1 according to the invention doesn't show this effect due to the symmetric cooling geometry. Most advantageously high-power, quasi-cw diode arrays 5 are used for side pumping the laser gain medium 2, for generating high peak-power pulses in the pulse energy regime of millijoules to Joules. The laser gain medium 2 is typically either a rod or a slab. The laser 1 according to the invention may be operated in a wide energy range with little thermal aberrations during operation. Therefore no means are necessary for compensation of thermal aberration, leading to an inexpensive, reliable laser device that may provide high-power laser light.

Figure 8:
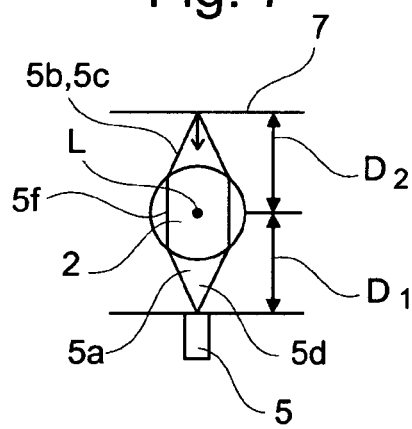
FIG. 8 depicts schematically the path of the laser beam of the arrangement according to FIG. 2 or 7.
Figure 9:
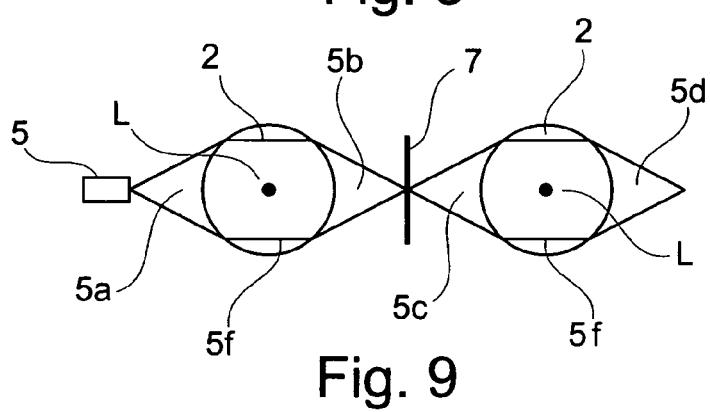
FIG. 9 depicts schematically the whole path of the laser beam of the arrangement according to FIG. 2 or 7.
Figure 20:
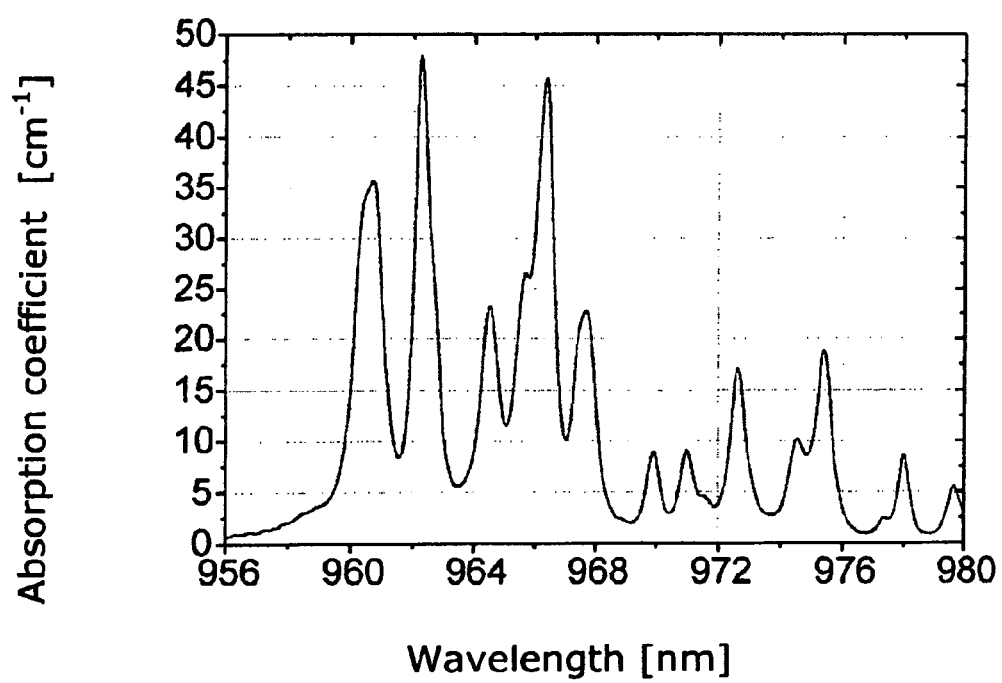
FIG. 20 depicts the absorption coefficient of Er:YAG material in function of the wavelength.

A further measure to provide a high performance operating laser device 1, in particular to achieve high intensity, high pulse energy and high pulse repetition rate, is disclosed with the following exemplary embodiment shown in FIGS. 7 to 9. FIG. 7 shows a cross-sectional view of a laser device 1 comprising a laser rod 2 arranged in the cooler 6. The contact faces 6c of the gain medium 2 with the heat conductive substance 6k are symmetrically arranged with respect to the longitudinal axis L of the laser gain medium 2. Laser 1 is a monolithic solid-state laser 1, comprising a laser resonator structure 3 as disclosed in FIG. 1, with a laser high reflector 4a on one end face of the laser rod 2, and with an output coupler 4b on the other end face of the laser rod 2. The laser rod 2 material includes e.g. Er:YAG. The laser rod 2 may for example have a diameter of 1 mm or 1.4 mm or 2 mm. The diode laser array 5 having a wavelength in the range of 760 nm to 815 nm or 955 nm to 985 nm. FIG. 20 shows the absorption coefficient of Er:YAG material in function of the wavelength. It is known to select the wavelength of the diode laser array 5 such that it corresponds to the maximum absorption of the laser active material 2. One additional aspect of the invention is that it has been found out that such a selection of the wavelength has the disadvantage that the pumping light of the diode laser array 5 is highly absorbed by the laser rod 2. This leads to the effect that the pumping light is already absorbed in the area of the side face 2a in the laser rod 2, so that only a reduced amount of pump light may enter the center of the laser rod 2, where most of the electrons should be activated. To overcome this effect it has been found out to select the main wavelength of the diode lasers 5 such that a reduced absorption occurs in the laser rod 2. Based on FIG. 20 this may be achieved by selecting the main wavelength of the diode laser 5 such that the main wavelength is shifted relative to a peak absorption of the laser gain medium 2, the main wavelength of the diode laser 5 might even be selected at a low or even a minimal absorption coefficient of the laser gain medium 2. Depending on the used low gain laser active material the deviation from the selected pump light wavelength to the pump light absorption peak can vary. For example the wavelength of the diode laser 5 may be shifted up to 15 nm and preferably up to 10 nm relative to the peak absorption line of the laser gain medium 2, which for example using Er:YAG is about 964 nm, the average center of a high absorption region. In addition the pumping light of the diode lasers 5 is advantageously guided as disclosed in FIGS. 7 to 9, to preferably achieve a uniformly illuminating of the laser gain medium 2 with the light of the diode laser 5.

The path of the pumping laser light 5 is schematically shown in FIGS. 7 and 8 in that the diode laser 5 emits pump light 5a which enters the laser gain medium 2, and which partially traverses the laser gain medium 2, and leaves the laser gain medium 2 as exiting pump light 5b. The wavelength of the pumping semiconductor laser is for example in the range of between 760 nm and 985 nm. The exiting pump light 5b being reflected at the reflector 7 of the cooler cavity 6d and being back scattered as reflected pump light 5c that enters again into the laser gain medium 2, which max partially traverses the laser gain medium 2 and which may even leave the laser gain medium 2 as a reflected exiting pump light 5d.

For example 100% of the total emitted energy of the diode laser 5 may enter the laser gain medium 2, 64% of the total emitted energy being absorbed in the laser gain medium 2, and 36% of the total emitted energy leaving the laser gain medium 2 as exiting pump light 5b. The exiting pump light 5b being reflected at the reflector 7 and around 36% of the total emitted energy enters the laser gain medium 2 in form of the reflected pump light 5c, and about 10% of the total emitted energy leaving the laser gain medium 2 as reflected exiting pump light 5d.

As disclosed in FIG. 8 the diode laser 5 and the reflector 7 are most preferably arranged in such a way with respect to the longitudinal axis L that there is equal distance D1, D2 between the longitudinal axis L and each of the diode laser 5 and the reflector 7. In other words, in a preferred embodiment, the length of the optical path between the pump source 5 and the longitudinal axis L is the same or about the same as the length of the optical path between the longitudinal axis L and the reflector 7. FIG. 9 discloses the path of the light of the diode laser 5 more clearly, such that the path of the reflected pump light 5c is shown for illustration purpose on the right side of the reflector 7 entering the laser gain medium 2 and leaving the laser gain medium 2 as exiting pump light 5d. The pump light 5a emitted by the diode laser 5 is entering the laser gain medium 2, and part of the pump light 5a is exiting the laser gain medium 2 as exiting pump light 5b. The exiting pump light 5b is reflected at the reflector 7, so that the reflected pump light 5c again enters the laser gain medium 2, and part of the reflected pump light 5c is exiting the laser gain medium 2 as reflected exiting pump light 5d. One advantage of the beam path of the pumping light disclosed in FIGS. 8 and 9 is that the laser gain medium 2 is preferably homogenously or about homogenously illuminated. One advantage of this kind of illumination of the laser gain medium 2 is that it allows achieving high power density and preferably also a good beam profile very similar to a Gaussian intensity distribution.

In the most preferred embodiment the wavelength of the pump source 5, which means the diode laser 5, is selected such with respect to properties of the laser gain medium 2, that between 30% to 70%, more preferably between about 50% to 65% of the pump light 5a is absorbed by the laser gain medium 2 and the rest exiting the laser gain medium 2 as exiting pump light 5b. Such a wavelength ensures that the gain medium 2 is homogenously illuminated. Most preferably the wavelength of the pump source 5 is selected in the range of between 955 nm to 985 nm, wherein the wavelength of the pump source 5 depends on doping material used, so that diode lasers 5 emitting in the wavelength required can be manufactured. If the gain medium 2 would comprise Holmium or Thulium, most preferably the wavelength of the pump source 5 is selected in the range of between 760 nm to 815 nm.

Most advantageously the contact area 6c and therefore also the heat flow 6f from the laser gain medium 2 to the cooler 6 is symmetrically with respect of the longitudinal axis L, as disclosed in FIG. 7, so that the light path 5a, 5b, 5c, 5d as disclosed in FIGS. 7 to 9 leads to the effect that the laser gain medium 2 is the hottest in the center, along the longitudinal axis L. This embodiment has the advantage that it is able to provide a high pulse energy and high power, and that temperature effects due to the warming up of the laser gain medium 2 are minimal. This embodiment has the additional advantage that it allows a high repetition rate, because the temperature effect due to the warming up of the laser gain medium 2 is small, and due to the effect that there is efficient cooling of the laser gain medium 2.

Figure 11A:
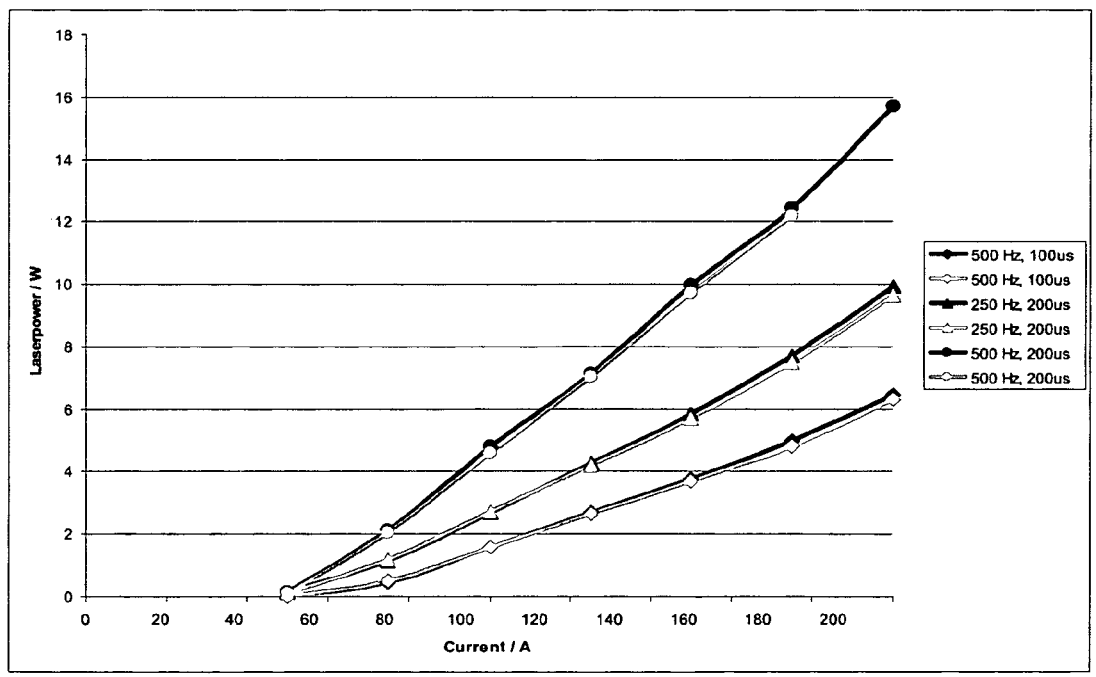
FIG. 11a depicts average optical output power as a function of current through the diode laser or semiconductor laser.

FIG. 11a shows the laser power, which is the average optical output power, as a function of the current through the diode laser 5 for different pulse repetition frequencies and for different pulse lengths. Two solid-state lasers 1 of identical construction are shown operated at 500 Hz with pulse lengths of 100 μs. Two solid-state lasers 1 of identical construction are shown operated at 250 Hz with pulse lengths of 200 μs. Two solid-state lasers 1 of identical construction are shown operated at 500 Hz with pulse lengths of 200 μs. FIG. 11a also shows that the two solid-state lasers of identical construction have only small variations, which means that the variation of the solid-state lasers according to the invention having identical construction is small.

Figure 11B:
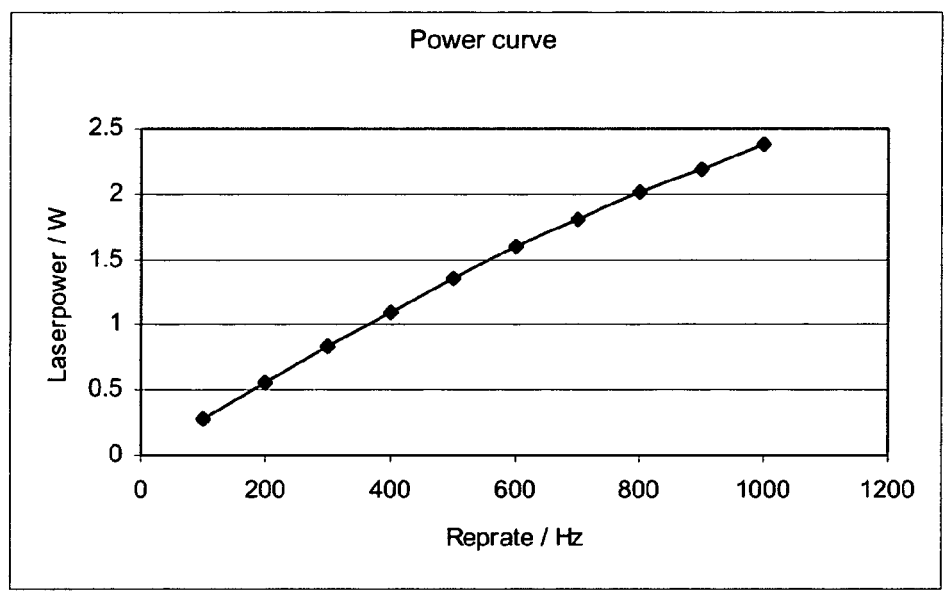
FIG. 11b depicts average optical output power as a function of repetition rate.

The solid-state laser 1 according to the invention creates relatively high laser power, which is the average optical output power, over a wide repetition rate, as disclosed in FIG. 11b. The solid-state laser 1 may be operated from about 100 Hz to 1000 Hz or more, as disclosed in FIG. 11b.

Figure 12:
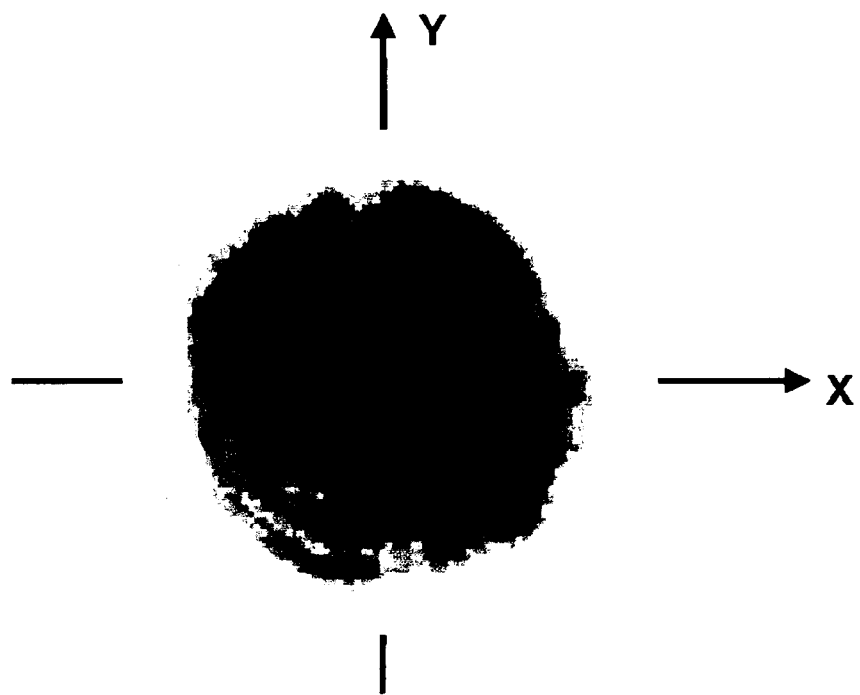
FIG. 12 depicts the energy density of an emitted laser beam, the laser rod being liquid cooled.
Figure 13:
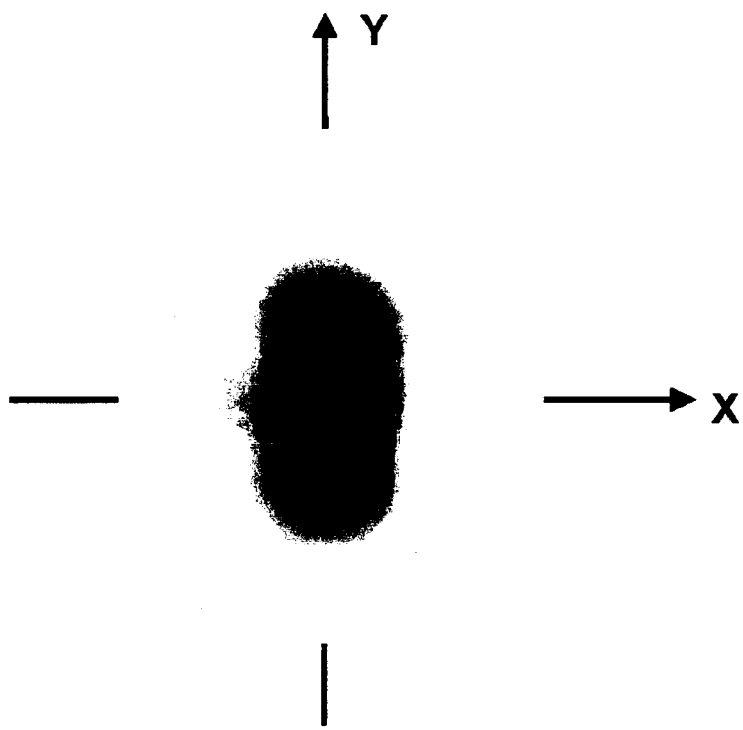
FIG. 13 depicts the energy density of a further emitted laser beam

The effect of the inventive measures described above can be seen in the laser mode profiles disclosed in FIGS. 12 and 13, showing the energy density of a laser beam B in a plane with directions x and y. FIG. 12 shows the energy density of an emitted laser beam B, the laser rod 2 being water cooled. FIG. 13 shows the energy density of an emitted laser beam B, the laser rod 2 being cooled by an arrangement according to FIG. 2. The effect of the efficient cooling is preferably that a low repetition rate and a low thermal loading as well as a high repetition rate and higher thermal loading doesn't distort the quality of the laser beam B. The laser gain medium 2 is most preferably of cylindrical shape or elliptical-cylindrical shape. The elliptical-cylindrical shape has the advantage that it is able to equalize a distortion of the laser beam caused by a conductive cooler 6 such as the coolers 6 disclosed for example in FIG. 2, 2a, 3 or 5 to 7, so that a laser beam B having an energy density of about the one disclosed in FIG. 12 may be achieved.

The embodiment according to FIGS. 7 to 9 has, by way of example, been described with a laser crystal 2 comprising an Er:YAG laser rod. All embodiments disclosed in FIGS. 1 to 16 may comprise laser rods of other suitable materials to achieve the same or similar effects as described in FIGS. 7 to 9. Most preferably the laser gain medium 2 is a low gain material such as Er:YAG, Er:YSGG, Ho:YAG or Ho:Tm:YAG.

Figure 14:
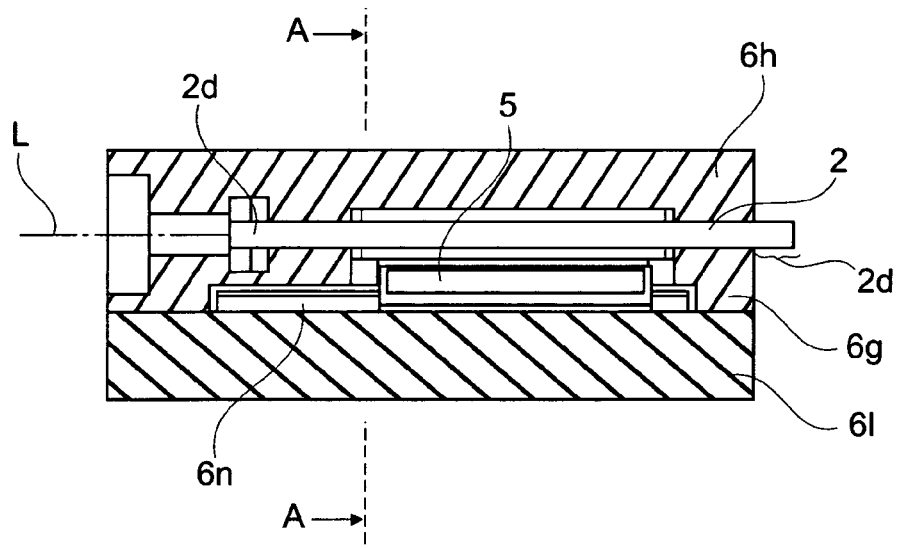
FIG. 14 depicts a cross-sectional view of a heat-sunk side-pumped solid-state laser along the line B-B of FIG. 15.
Figure 15:
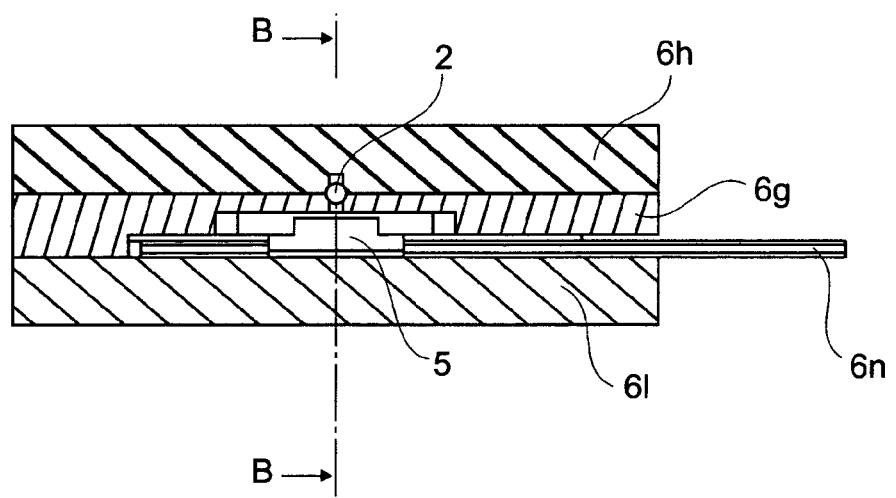
FIG. 15 depicts a cross-sectional view of the laser according to FIG. 14 along the line A-A.

FIG. 14 shows a cross-sectional view of a side-pumped solid-state laser 1. The laser 1 comprising a laser gain medium 2 fixed between a lower part 6g and an upper part 6h of a cooler 6. The laser 1 also comprising a base plate 6l. An array of diode lasers 5 are arranged along the laser gain medium 2 for pumping the same. The array of semiconductor lasers 5 is fixed on a plate 6n such as a printed circuit board. As disclosed in FIG. 14 the laser gain medium 2 has most preferably free ends 2d which are not arranged within the cooler 6, whereby the length of the free ends 2d in direction of the longitudinal axis L is preferably about 1 mm. The free ends 2d act as stress reducing elements to improve lasing stability and decrease thermal lensing effects which leads in turn to high laser stability over a wide working range. Most preferably, all embodiments disclosed in FIGS. 2, 2a, 3, 5, 6 and 7 comprise such free ends 2d as disclosed in FIG. 14, the free end having a length of preferably about 1 mm. FIG. 15 shows another cross-sectional view A-A of the embodiment according to FIG. 14 showing the laser gain medium 2, which has the shape of a rod, and which is fixed between the lower and upper part 6g, 6h of the cooler 6. The pump source 5, a diode laser array, is arranged beside the laser gain medium 2.

Figure 16:
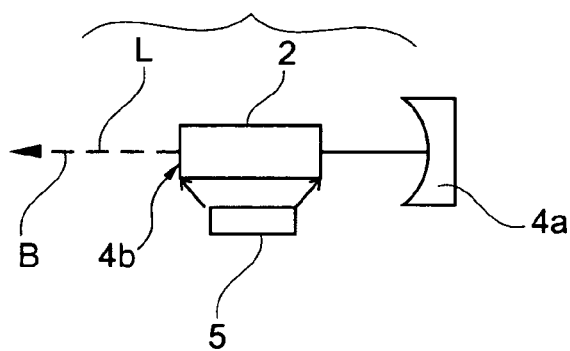
FIG. 16 depicts a diagram of a semi-monolithic, side-pumped solid-state laser.

FIG. 16 shows a laser resonator structure 3 comprising a laser gain medium 2, a pump source 5, an output coupler 4b and a spaced apart laser high reflector 4a. Such an embodiment might be necessary if the totally reflecting laser mirror 4a disclosed in FIG. 1a, which is arranged on one of the end faces of the main medium 2, becomes too hot because of high intracavity power, so that instead of the reflecting laser mirror 4a arranged on the one of the end faces, a spaced apart reflecting laser mirror 4a is used.

Figure 17:
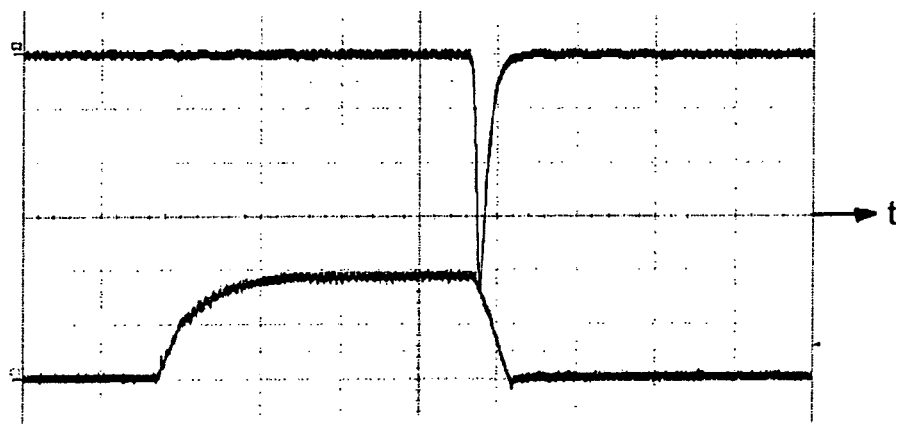
FIG. 17 depicts a time diagram of the current driving the pumping semiconductor laser and of the emitted laser light; driving the pumping semiconductor laser and of the emitted laser light.
Figure 18:
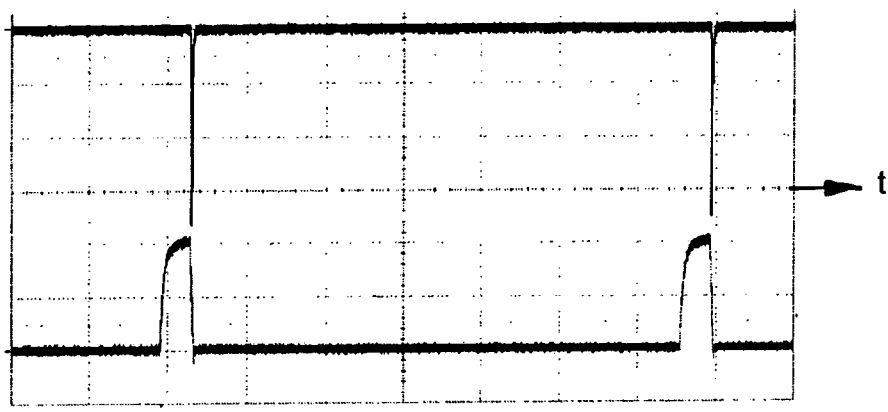
Figure 19:
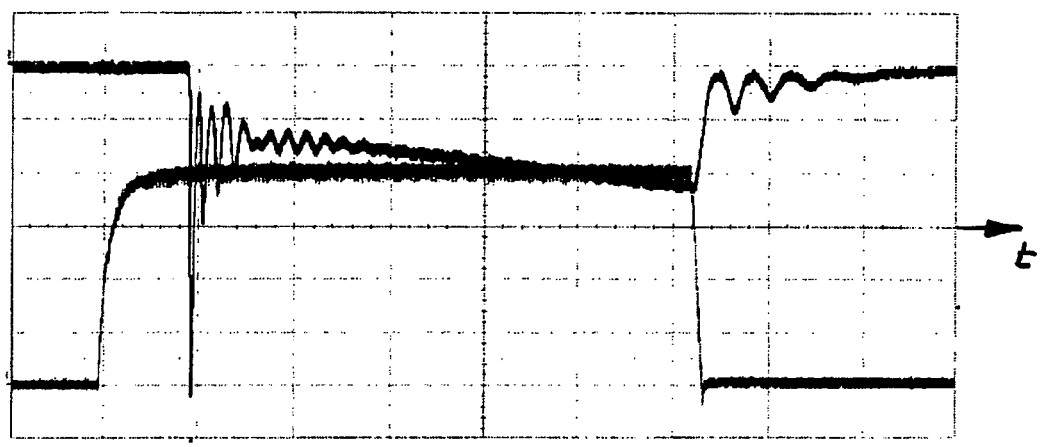
FIG. 19 depicts another time diagram of the current driving the pumping semiconductor laser and of the emitted laser light to operate the laser in CW-mode.

FIG. 17 shows the pump light 5 (lower curve) and the emitted laser beam B (upper curve) versus time. The pump light 5 pumps the laser gain medium 2 up to the laser gain medium 2 emits a laser beam B. In the example disclosed the pump light 5 is stopped as soon as the laser gain medium 2 emits the laser beam B, which leads to very short laser pulses of between 1 to 5 μs pulse length. Longer pulses can be achieved by prolonging the pump light 5 so that the laser gain medium 2 is pumped during a longer period of time, which leads to longer pulses of the laser beam B. FIG. 18 shows the pump light 5 (lower curve) and the emitted laser beam B (upper curve) versus time over longer period of time. The pump light 5 may, for example, be regularly emitted, as disclosed in FIG. 18, so that a laser pulse B is regularly emitted. FIG. 19 shows another time diagram of the current respectively the pump light 5 (lower curve) driving the pumping diode 5 and of the emitted laser light to operate the laser in CW-mode (continuous wave mode).

Figure 21:
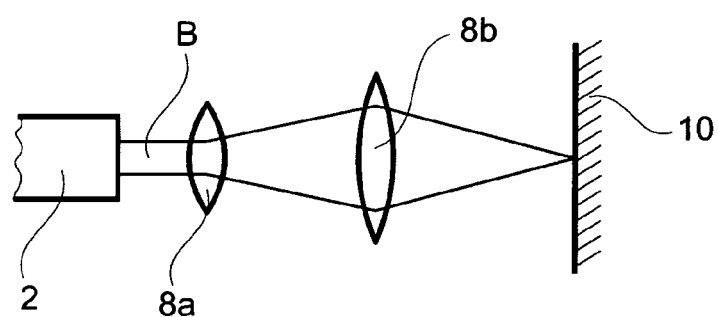
FIG. 21 depicts a monolithic solid-state laser followed by lenses.
Figure 22:
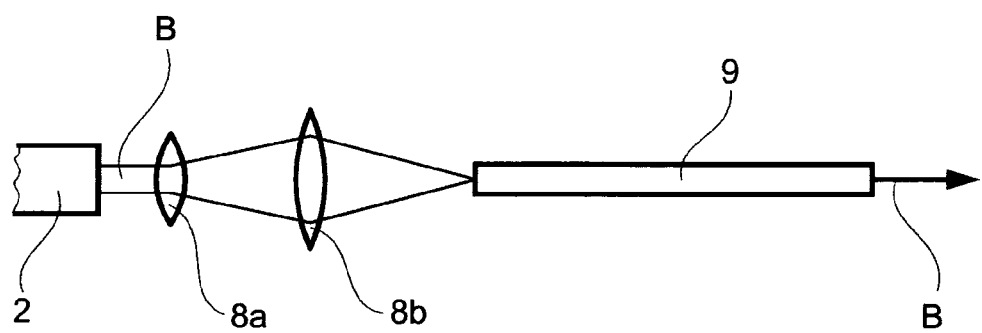
FIG. 22 depicts a monolithic solid-state laser followed by a fiber.

FIG. 21 shows a side view of the monolithic solid-state laser 1, where the laser beam B is spread and focused by lenses 8a, 8b, to focus the laser beam B onto a target 10. FIG. 22 shows a side view of the monolithic solid-state laser 1, where the laser beam B is expanded and focused by lenses 8a, 8b, to focus the laser beam B into an optical fiber 9. In a preferred embodiment the optical fiber 9 has a diameter in the range of 100 µm to 250 µm, most preferably of less or equal 200 µm, and the laser beam B entering into the optical fiber 9 has in a preferred embodiment a diameter of less or equal 100 µm. At the exit or following the exit end of the optical fiber 9 an additional lens may be arranged. The laser gain medium 2 according to the invention having a cross sectional area of less than 7.5 mm² has the advantage that the exiting laser beam B may be focused to a diameter of less or equal 100 µm. Known laser gain medium 2 have a diameter of 3.5 mm or even more, which causes the problem that the laser beam B of such laser gain mediums 2 can only be focused to a diameter of about 400 µm, which doesn't allow creating a laser beam of high intensity. In addition optical fibers 9 having a diameter in the range of 300 µm to 500 µm were required. The solid-state laser 1 according to the invention therefore has the advantage that a laser beam B of high intensity may be emitted, and because of the small diameter of the beam, a small optical fiber 9 having a diameter of for example less or equal 200 µm may be used. Therefore a laser beam B of relatively high intensity may pass the optical fiber 9.

In a preferred embodiment the laser 1 according to the invention having a wavelength in particular between 1700 nm and 3200 nm. Most preferred a wavelength of about 2950 nm is used because this is a major local maximum in the water absorption spectrum in the MIR (mid-infrared) range. There is another water absorption peak in the ultra violet range but this wavelength is not save for treating or ablating life tissue. Most preferably, the gain medium 2 may comprise an Erbium-doped crystalline laser rod for generating laser light in a range between 2.73 and 2.95 µm. The laser light can be generated in the TEM00 mode and strongly focused to overcome thermal effects. Temporal pulse width control can be used to attain a uniform temporal pulse pattern. The diode or semiconductor laser light pump 5 can comprise a diode array, and the diode array can be optically aligned to side pump the gain medium.

The diode side pumped Erbium doped crystalline laser gain medium 2 may emit at wavelengths between 2.73 and 2.95 The pumping may be accomplished by e.g. InGaAs diode lasers configured as bars or arrays emitting at between 955 to 985 nm, and can be delivered in either a CW (continuous wave) or a QCW (quasi-continuous wave) mode of operation, at power levels that may begin at 40 W peak power. With an optimized output coupling, the light-to-light efficiency can be at least 10% and can reach a magnitude up to 35%. One of the embodiments of this invention is that these efficiency magnitudes are higher than those which may have been previously attained, owing to the inventive design which seeks to minimize thermal effects and intracavity losses and to optimize the beam path of the pump light to enable high energy pulses or CW operation of the laser.

In a further preferred embodiment the laser 1 according to the invention having a wavelength in particular between 1675 nm and 2100 nm, whereby the gain medium 2 comprises a Holmium-doped and/or a Thulium doped crystalline laser rod for generating laser light in a range between 1.67 and 2.1 µm. The laser light can be generated in the TEM00 mode to overcome thermal effects. Temporal pulse width control can be used to attain a uniform temporal pulse pattern. The diode side pumped Holmium-doped and/or a Thulium doped crystalline laser gain medium 2 may emit at wavelengths between 1.67 and 2.1 µm. The pumping may be accomplished by e.g. AlGaAs diode lasers configured as bars or arrays emitting at between 760 to 815 nm or by e.g. GaSb laser diodes emitting at between 1600 to 2050 nm, and can be delivered in either a CW (continuous wave) or a QCW (quasi-continuous wave) mode of operation, at power levels that may begin at 20 W peak power. With an optimized output coupling, the light-to-light efficiency can be at least 10% and can reach a magnitude up to 85%.

A suitable optical gain material 2 may include the following crystals: Er:LiYF$_4$ (Er:YLF) emitting at 1.73 µm on the Er$^{3+4}$I$_{13/2}$⇒$^4$I$_{15/2}$ transition; Er:LiYF$_4$ emitting at 2.80 µm on the Er$^{3+4}$I$_{11/2}$⇒$^4$I$_{13/2}$ transition; Er:Y$_3$Sc$_2$GasO$_{12}$ (Er:YSGG) emitting at 2.79 µm on the Er$^{3+4}$I$_{11/2}$⇒$^4$I$_{13/2}$ transition; Er:Gd$_3$Sc$_2$GasO$_{12}$ (Er:GSGG) emitting at 2.8 µm on the Er$^{3+4}$I$_{11/2}$⇒$^4$I$_{13/2}$ transition; Er:Gd$_3$GasO$_{12}$ (Er:GGG) emitting at 2.82 µm on the Er$^{3+4}$I$_{11/2}$⇒$^4$I$_{13/2}$ transition; Er,Tm:Y$_3$Al$_5$O$_{12}$ (TE:YAG) emitting at 2.69 µm on the Er$^{3+4}$I$_{11/2}$⇒$^4$I$_{13/2}$ transition; Er:KYF$_4$ emitting at 2.81 µm on the Er$^{3+4}$I$_{11/2}$⇒ transition; Ho, Yb:KYF$_4$ emitting at 2.84 µm on the Ho$^{3+5}$I$_6$$^5$I$_7$ transition; Er:Y$_3$Al$_5$O$_{12}$ (Er:YAG) emitting at 2.94 µm on the Er$^{3+4}$I$_{11/2}$⇒$^4$I$_{13/2}$ transition; Er:Y$_3$AlO$_3$ (Er:YALO) emitting at 2.71 µm on the Er$^{3+4}$I$_{11/2}$⇒$^4$I$_{13/2}$ transition; Er:KGd(WO$_{4s}$(Er:KGW) emitting at 2.8 µm on the Er$^{3+4}$I$_{11/2}$⇒$^4$I$_{13/2}$ transition; Er:KY(WO$_{4s}$ (Er:KYW); Er:Al$_2$O$_3$ emitting on Er$^{3+4}$I$_{11/2}$⇒$^4$I$_{13/2}$ transition; Er:Lu$_3$O$_3$ emitting at emitting at 2.7 µm on the Er$^{3+4}$I$_{11/2}$⇒$^4$I$_{13/2}$ transition; Er:CaF$_2$ emitting at 2.75-2.85 µm on the Er$^{3+4}$I$_{11/2}$⇒$^4$I$_{13/2}$ transition; Cr,Tm,Er:Y$_3$Al$_5$O$_{12}$ (CTE:YAG) emitting at 2.7 µm on the ER$^{3+4}$I$_{11/2}$ transition; Er:BaLu$_2$F$_8$ emitting at 2.8 µm on the Er$^{3+4}$I$_{11/2}$⇒$^4$I$_{13/2}$ transition; Er:BaY$_2$F$_8$ (Er:BYF) emitting at 2.7 µm on the Er$^{3+4}$I$_{11/2}$⇒$^4$I$_{13/2}$ transition; and Cr:ZnSe emitting at 2-3 µm.
CTH:YAG or Cr:Tm:Ho:YAG emitting at 2080 nm, 2097 nm and 2130 nm
Ho:YAG emitting at 2097 nm
Ho:YLF emitting from 1850 to 2075 nm
Ho:Tm:YAG emitting from 2091 to 2097 nm
Tm:YAG emitting at 2013 nm
Tm:Cr:YAG emitting at 2017 nm
Tm:YLF emitting from 1675 to 2050 nm
Tm:YAP emitting from 1965 to 2020 nm
Tm:Lu:YAG emitting at 2020 nm Another embodiment of the side diode pumped erbium lasers and Tm, Ho, Yb:KYF$_4$ laser is that when operated in pulses, the pulsed format is highly repetitive in time and intensity. This performance can for example facilitate precise and predictable cutting, and can improve cutting efficiency. In dental and medical applications, this feature is consistent with less heat or thermal denaturation of the tissue, which can provide for quicker healing.
This invention is not limited to Er doped, Ho doped or Tm doped low gain laser active materials, but also high gain laser active materials may be used, such as Nd:YVO$_4$, Nd:YAG, Er:Glass, and many others. In the case of using a high gain laser active material the advantage of the invention is the very good robustness against disadjustment caused by shock events, vibration and disadjustment over time due to thermal effects.

Due to their efficient interaction with biological tissue and water, the laser according to the invention is for example useful as surgical instruments, in the areas of, for example, tissue surgery, tissue cutting, tissue ablation, dental surgery, orthopedic surgery, bone cutting and soft tissue surfacing.

Figure 23:
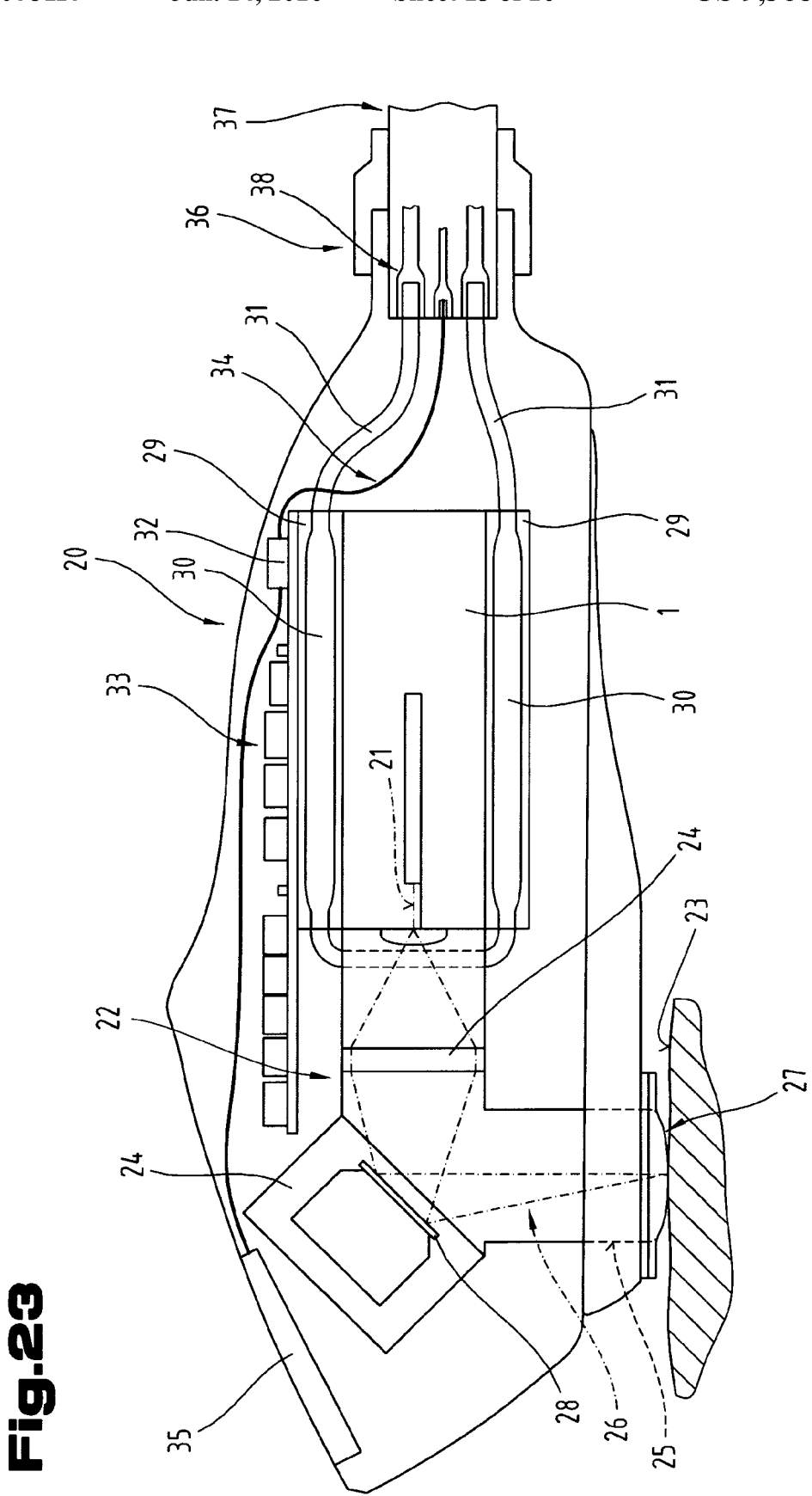
FIG. 23 depicts a handheld device which is attachable to a table top unit.

FIG. 23 discloses a treatment device according to the present invention, where a handheld device 20 is attachable to a table-top unit. The handheld device 20 comprises a solid-state laser 1 according to the present invention, which laser emits a laser beam 21 that is directed along an optical pathway 22 to the target surface 23. The optical pathway 22 comprises the solid-state laser 1, a laser output coupler that is e.g. embodied as dispersant lens, a beam formation and deflection unit 24, which may be separated into two parts, a beam formation and a beam deflection part. The optical pathway 22 ends at the contact window 25 where the formed laser beam 26 exits the handheld device 20 and penetrates the target surface 23. This contact window is preferably sealed with a highly transparent window, to let the laser beam with a specific wavelength pass the window without energy losses or beam intensity distribution. The contact window 25 furthermore defines a specific region on the target surface 23 in which region the formed laser beam 26 can penetrate the target surface 23 and thus defines a treatment area on the target surface. As this treatment device 20 may be used in medical applications and therefore a contact with live tissue is possible, a cleaning and/or sterilisation of the contact window between each treatment is required. Therefore the covering 27 of the contact window 25 has to withstand aggressive cleaning media, furthermore the covering 27 may be detachable from the handheld device 20 and maybe cleaned separately or discarded, attaching a new covering 27 for each treatment. The covering 27 may be a snap-on like device, allowing the user to attach and detach the covering 27 without having to touch it, thus providing a high amount of sterility.

The beam formation and deflection unit 24 performs a widening of the coherent laser beam 21 emitted by the solid-state laser 21, in order to form and focus the laser beam within the outlet opening 25, respectively within the target area on the target surface 23. Therefore a selectively movable mirror 28 is arranged within the optical pathway 22 allowing the deflection of the laser beam. An example of a preferred embodiment of the beam formation on deflection unit is disclosed in the WO 2009/150210.

During the operation of the solid-state laser 1, waste heat is generated, which has to be removed from the solid-state laser 1, in order to keep the laser operational. Therefore a cooling unit 29 is arranged on the solid-state laser 1 which cooling unit 29 comprises a cavity 30, wherein a cooling liquid circulates. The cooling unit 29 is connected via cooling liquid transportation tubes 31 to a cool liquid circulation system in the table-top unit. Therefore a huge amount of thermal energy can be removed from the solid-state laser 1 keeping the laser within safe operation parameters, even for a long operation on a high duty cycle.

For controlling the solid-state laser 1 and the beam formation and deflection unit 24a control unit 32 is arranged within the handheld device 20, which control unit 32 further comprises at least one high current capacity buffer 33 which is embodied e.g. as tantalum or niobium capacitors. The control unit 32, respectively the high current capacity buffer 33, is connected via an electrical supply line 34 with a power supply in the table-top unit, which power supply provides electrical energy for charging the current buffer 33.

The control unit 32 may be connected with an operation control switch unit 35 that enables the user of the handheld device 20 to control the basic operation of the solid-state laser, e.g. control the emission of the laser beam.

One major disadvantage of prior art laser based treatment systems is that the maintenance of the laser is a very difficult task. Usually a service technician has to come on site, because previous laser systems, once configured and operational, are not embodied to be shipped to a maintenance station, as this shipment might severely damage the laser system. Due to the robust embodiment of the solid-state laser according to the present invention, the laser does not require specific careful treatment and therefore an exchange, especially shipping to a maintenance station, can easily be done without having the danger of damaging the laser. Therefore an advantageous embodiment of the treatment device is that the handheld device 20 comprises a detachable connector 36, with which the handheld device 20 may be connected via a flexible hose 37 with a table-top unit. The connector 36 may be a screw type or bayonet type connector means, further having specifically arranged and aligned connector means 38 for connecting the tube lines 31 and the supply lines 34 within the handheld device 20, with respective tubes and lines within the flexible hose 37. Another advantage of this embodiment is that individual handheld devices, with solid-state lasers 1 emitting on specific wavelengths, can be connected to the tabletop unit. Therefore the treatment can be conducted using the specifically selected wavelengths without requiring multiple treatment devices to be available, by simply just reusing, respectively connecting the table-top unit that provides operational power and operation media supply, to a various selection of individually designed handheld devices.

Figure 24:
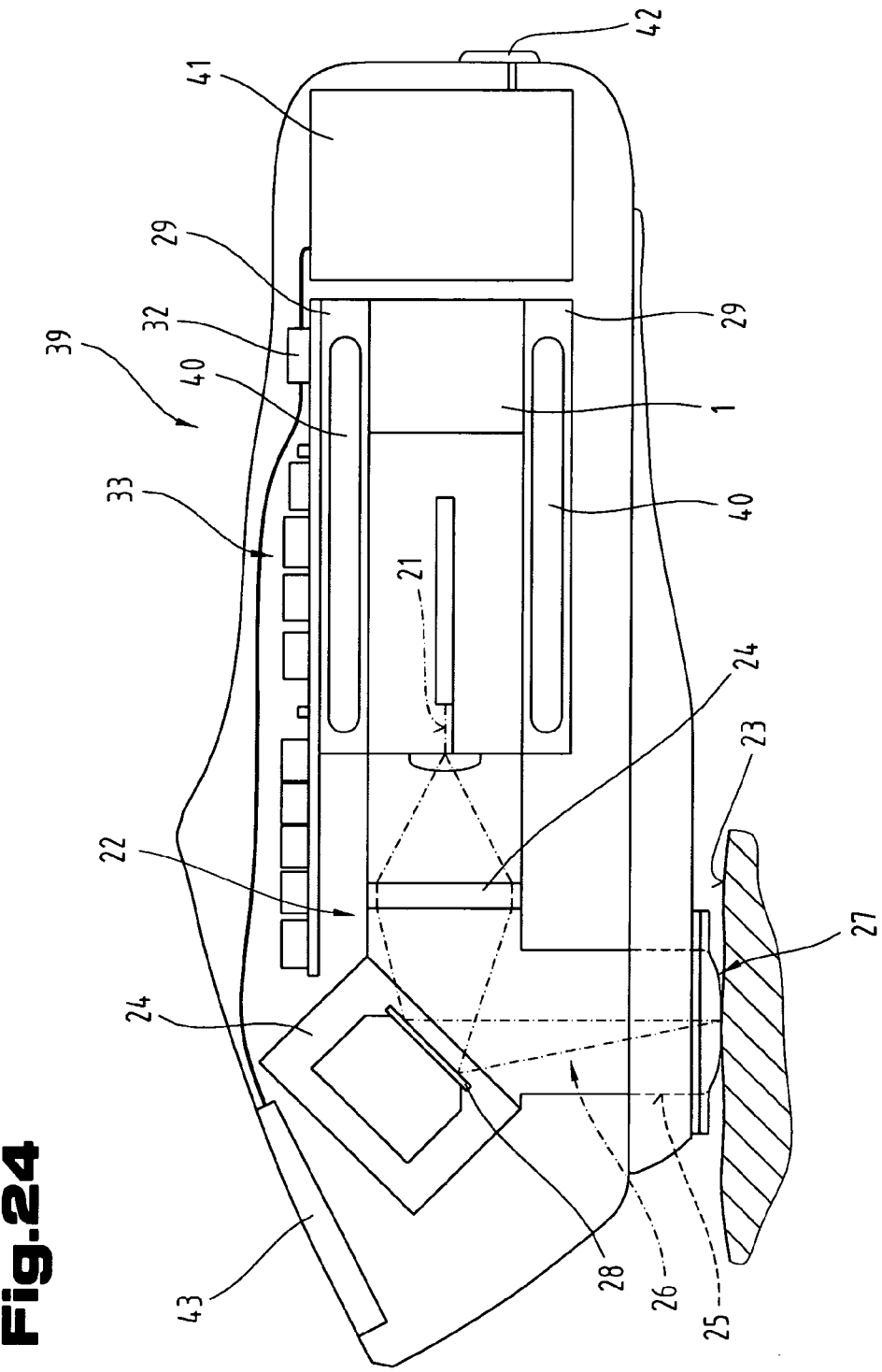
FIG. 24 depicts a stand-alone handheld device.

FIG. 24 discloses another embodiment of the treatment devices, especially a stand alone handheld device 39 is disclosed. The basic functional elements are the same as described in the previous FIG. 23, especially the solid-state laser 1 is embodied according to the present invention. As the device 39 is a stand alone device, the cooling of the solid-state laser 1 cannot be realized by a liquid cooling system, but has to be done entirely within the handheld device 39. Therefore the cooling unit 29 is embodied as solid-state cooling unit which may for example comprise a free air cooling means. As the number of treatments that can be done with a mobile handheld device 39 is limited, e.g. due to energy supply reasons, the repetition rate of the laser unit 1 and therefore the amount of heat generated by the solid-state laser, a free air cooling might be sufficient to keep the solid-state laser within normal operation parameters. According to one embodiment the cooling unit 29 may comprise material 40 that has a reversible phase state change within the operation temperature range of the laser. As it is known, a phase state change of a material requires much more thermal energy than a heating up within one phase state. For example paraffin has usually a phase state change at a temperature of about 42°, which is very suitable for taking over the excess heat of the solid-state laser 1. During the operation pause, the heated up paraffin emits the stored heat to the ambient, thus performing a phase state change from liquid to solid and therefore preparing itself for the next usage.

The energy for operating the laser and the control unit 32 is provided by an electrical energy storage means 41, which is e.g. embodied as Li-Ion or Lithium polymer secondary cell. After performing a number of treatment operations, the handheld devices 39 is connected to an electrical supply system via a connection port 42, thus recharging the electrical storage means 41 for the next operation cycle.

In order to configure the standalone handheld device 39 for the requirements of the treatment to be conducted, the handheld device further comprises a user interface 43, preferably with a display and an input device. This user interface 43 is connected to the control unit and allows an individual configuration of the laser operation parameters, without requiring the handheld device 39 to be connected with an external control unit.

Figure 25:
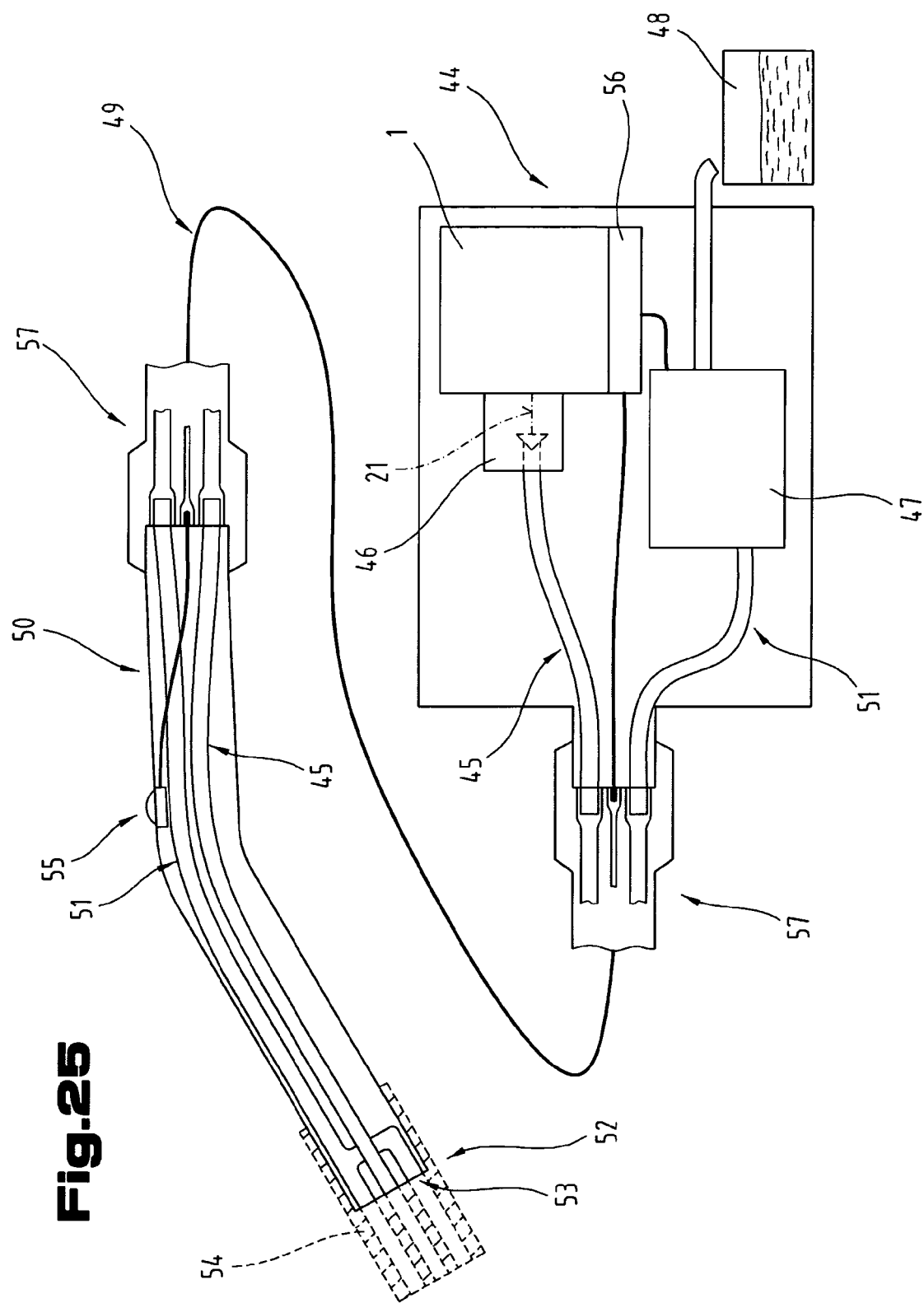
FIG. 25 depicts a treatment device.

FIG. 25 discloses a treatment device, comprising a solid state laser 1 according to the present invention, arranged in a housing 44. The solid state laser 1 emits a laser beam 21 which is directed into a light guiding element 45 by an optical coupling device 46. This optical coupling device 46 can be based on effects of non-imaging or imaging optics, fiber concentrator or tappered fibers. The light guiding element 45 maybe e.g. a single fiber or multi fiber element, where the objective of the optical coupling device 46 is, to direct the laser beam 21 with a diameter of approximately 60% of the fiber diameter into the light guiding element 45, which has a diameter of approximately 150 to 550 µm for a single fiber element or into a multiple number of 75 to 200 µm fibers in case of a multi fiber light guiding element 45.

The housing 44 may further comprise a device for generating a pressurized gas and/or a device for generating a pressurized liquid. Relative to the surrounding, a pressurized gas can have a positive or negative pressure, where a gas with a positive pressure can be used for blowing away ablated material at the target area, a pressurized gas with a negative relative pressure can be used to suck away ablated material from the target area, including liquids that are present at the target area. In FIG. 25a device for generating a negative pressurized gas 47 is disclosed, which incorporates a guide to a waste compartment 48, thus allowing ablated material to be sucked away from the target area, where the laser penetrates the target surface, and to be collected in the waste bin 48 for a process safe removal.

At least the light guiding element 45 is connected to a handheld device 50 via a flexible hose 49. The flexible hose may be a fiber enhanced flexible tube, wherein at least the light guiding element 45 is arranged. For simplification reasons, the flexible hose with the various lines arranged within is sketched in FIG. 25 as single line. The objective of the flexible hose is to protect the lines arranged within, in order to provide a free movement of the handheld device 50 arranged apart from the housing 44. In another embodiment, the flexible hose may be composed of the optical light guiding element itself, in that the guiding element comprises a protective and flexible covering. This provides a flexible hose with a very low diameter and a high degree of flexibility. The handheld device 50 is e.g. a solid hand peace, similar to a dentist drilling device. Inside the handheld device 50, the light guiding element 45 and as in the example of FIG. 25, a duct 51 for providing pressurized liquid and/or pressurized gas, is arranged at the working end 52 of the handheld device 50. At the working end 52, an outlet port 53 is arranged, which outlet port is connected to the light guiding element 45 and a further outlet port is connected to the duct 51, where in the depicted embodiment, the outlet port connected to the duct is arranged around the outlet port connected to the light guiding element 45, thus providing a working tip where the ablated material is sucked away around the working area, where the laser beam penetrates the target surface.

For sterilization reasons, a working cap 54 may be placed on top of the working tip 52 extending the outlet ports, and inhibiting a contact of the working tip, especially the end of the light guiding element 45 with the target surface or with ablated material. This is quite important for clinical applications, where a transfer of biological material from one patient to another patient must be avoided. The protective cap 54 may be a single use disposable device or a reusable, but thoroughly cleanable device, thus reducing the cleaning effort to maintain the handheld device 50 sterile.

The handheld device 50 may further comprise an operation switch 55 which is connected via the flexible hose to a control unit 56 within the housing 44. This operation switch 55 can be e.g. a simple ON/OFF switch, controlling the operation of the solid state laser 1 and the device for generating pressurized liquid and/or pressurized gas. Other control switches maybe possible, providing a more sophisticated possibility, on how the user can control the operation of the various devices for performing the treatment.

According to an embodiment of the present invention, the handheld device 50 is detachable from the solid state laser 1. Therefore the handheld device 50 and/or the housing 44 may comprise a connector means 57 which allows to disconnect the handheld device 50 from the flexible hose 49, or to disconnect the flexible hose 49 from the housing 44. Another embodiment may be possible where only connector means 57 is attached to the flexible hose, thus removing the one piece handheld device and flexible hose from the housing. As one operation area of the treatment device are clinical applications, a thorough cleaning and sterilization of each component that got in contact with biological material has to be conducted. In case the light guiding element 45 is of a high sophisticated and very expensive material, like Sapphire, using a protective cap 54 is very suitable, as it reduces the requirements for cleaning the handheld device 50 and the ducts inside the flexible hose 49. Furthermore the handheld device 50 may be a single use device, so it may be disconnected from the flexible hose, be discarded, and replaced with e new handheld device for the next usage. On the other hand, the light guiding element 45 may be of $SiO_2$, which is a very cheap material for light guiding elements, it would be a suitable solution to discard the handheld device 50 together with the flexible hose 49, and using new components for each treatment. Disconnecting the handheld device 50 from the flexible hose 49, and the flexible hose from the housing 44 individually, provides the possibility to perform individual sterilization procedures, the handheld device may for example be sterilized in an autoclave unit, the flexible hose may be submerged in a disinfection solution.

The connector means 57 provides individual connection parts for a proper aligning the ducts and the light guiding element, so that a liquid and/or gas tight connection is established. Furthermore there are no connection losses when the laser beam is handed over from the flexible hose 49 to the handheld device 50. The same applies to the connector means connecting the flexible hose with the housing 44.

FIG. 26a discloses a simplified depiction of the working tip, where a duct supplies pressurized liquid to the tip, which, together with the ablated material, is sucked away by a duct providing pressurized gas with a negative relative pressure. In the depicted embodiment the light guiding element 45 is embodied as multi fiber light guiding element, comprising a number of single light guiding fibers 61. A duct 58 delivers pressurized liquid to the working tip end 59, another duct 60 provides pressurized gas with a negative relative pressure and has its outlet opening also on the working tip end 59. The single fibers 61 of the light guiding element 45 are arranged around the duct, providing pressurized gas. The duct for providing pressurized liquid 58 surrounds the fibers 61, therefore the pressurized liquid is transported between the outer perimeter of the duct, providing the pressurized gas, and the outer perimeter of the duct, providing pressurized liquid, thus surrounding the single light guiding fibers 61. When the laser is operational, each of the single fibers 61 emits a laser beam to the target surface. Liquid provided by the duct 58 is also directed to the target area, washing away the ablated material. To remove the ablated material from the target area, the provided liquid together with the ablated material is sucked into the duct 60 providing the negative relative pressurized gas and therefore keeping the target area clean and avoiding a potential tissue damage, due to laser beam scattering or insertion of excessive heat.

FIG. 26b shows another embodiment of the working tip ending 59 in front view. A single fiber light guiding element 45 is arranged in the middle of the working tip end 59, surrounded by outlet ports for pressurized liquid 62 and outlet ports for pressurized gas 63 with a negative relative pressure. This has a similar function to the one embodiment described in FIG. 26a, as liquid is used to purge the target area and then the liquid, together with the ablated material, is sucked away by a duct 63 by means of a negative pressurized gas.

FIG. 26c discloses another embodiment of the working tip end 59 in front view, where several fiber endings 61 of the light guiding element are arranged around ducts, one for providing pressurized liquid 62 and one for providing pressurized gas 62 with a negative pressure. Furthermore there may be an illumination means 64 arranged on the tip end, which light emitting element may be embodied as a light emitting diode, or preferably this illumination means 64 is embodied as a separate light guiding element, or could be one fiber of the light guiding element, providing the laser beam. Furthermore another light guiding element or also a fiber of the light guiding element providing the laser beam, can be used as image gathering means 65, directing the image to an image analysis and processing means in the housing and thus providing the operator a clear view of the target area, which would not be possible with an eyes only based monitoring of the target area.

The working tip end 59 can further comprise a sound transducer, respectively a working tip of a sound transducer, or electrodes of a radio frequency transmitter, both providing further application possibilities to ablate material in the target area.

FIG. 26d discloses a side view of the working tip end 59, where the light guiding element 45 protrudes the top surface of the working tip end, and where the light guiding element further has a shaped ending, such as a skew 66. The skewed surface may be covered with a dielectric layer or a layer arrangement or operates based on total internal reflection, so that the laser beam transported by the light guiding element 45, leaves the element in an angle different from the parallel axis of the light guiding element, e.g. normal to the parallel axis. This embodiment enables an ablation of material different from the working direction, especially material can be ablated on areas beside the working direction of the working tip.

For completeness, further preferred forms of embodiment are as follows:

I.)
A medical laser device,
comprising a laser described in this application,
comprising a coupling unit allowing the optimum coupling of the laser light into at least one light-guiding element (e.g. fiber optic, hollow fiber optic, articulated mirror arm),
coupled to at least one light-guiding element, which is designed to be interchangeable and possibly also sterilisable or as a disposable component
to treat pathogenic clumps in the body (gallstones, arterial calcifications, kidney stones, bladders stones etc) in that the light guiding element approaches the clumps in the body in order to destroy them with high pulse energies or high energy pulses, either through the explosive evaporation of water in the clump or through shockwaves caused by the explosive evaporation of water or tissue containing water directly in front of or around the clump.
The advantage of using this laser is that the pulse energy, the pulse duration and the intensities (pulse energy per unit of time) as well as the repetition rate can be adjusted within a broad range in order to adapt the treatment individually to the patient. A further advantage of the laser described here is the reduction in thermal destruction caused by commercially available flash light pumped laser systems or poorly directed ultrasonic energy.

II.)
A medical laser device,
comprising a laser described in this application,
comprising a coupling unit allowing the optimum coupling of the laser light into at least one light-guiding element (e.g. fiber optic, hollow fiber optic, articulated mirror arm),
coupled to at least one light-guiding element, which is designed to be interchangeable and possibly also sterilisable or as a disposable component
(at least one) of these light-guiding elements is connected to a handheld device, which may be interchangeable and possibly also sterilisable or designed as a disposable component
the handheld device possibly comprises a further coupling unit, which optimally couples the laser light into at least one of the light-guiding elements and then on to the point to be treated or into a light-guiding element, which may be interchangeable and possibly also sterilisable or designed as a disposable component
in addition to at least one of these light-guiding elements, possibly also an accompanying tube for fluids and/or gases which are pumped away from the device and/or sucked in and/or electrical leads (e.g. switching contact signals, indication signals . . . ) and/or optical lines for transmitting data from the point to be treated or to conduct light (illumination, laser light, target lasers . . . ) to the point to be treated.
for the treatment of diseases of the (animal or human) eye, such as, for example, glaucoma and cataract (the appurtenant treatment is cataract surgery with phacoemulsification (breaking down of the lens) with subsequent insertion of an artificial lens), increased inner ocular pressure (the appurtenant treatment is trabeculotomy or iridectomy) which usually leads to glaucoma, the treatment of the vitreous body for "vitreous floaters" or clouding of vitreous body (the appurtenant treatment is vitrectomy). Last but not least lens correction can be carried out with this laser.
The advantage of using this laser is that the pulse energy, the pulse duration and intensities (pulse energy per unit of time) as well as the repetition rate can be adjusted within a broad range in order to adapt the treatment individually to the site to be treated. For example, during phacoemulsification, with a laser the lens is broken down much more gently than with commercially available ultrasonic breakers or flash light pumped solid-body lasers, as less thermal energy is applied and it can be better regulated. As long as lens tissue in the area of the lens is broken down which is not in the vicinity of healthy tissue or in the interior of the lens to be broken down, work can be carried out with high pulse energies and high repetition rates. As soon as an area at the edge of the lens or in the vicinity of healthy tissue is approached, the laser energy and the repetition rate can be reduced in order to work more precisely. The lower repetition rates prevent an accumulation of thermal energy in the tissue and thereby its destruction. As with ultrasound, the lens body is broken down by shock waves which in the laser are caused by cavitation bubbles. If only one or a few fibers are taken to the tissue to be removed, the cavitation bubbles are larger and/or longer than when several fibers are used. This risks a too great dissipation of the shock wave into healthy tissue. Complete, gentle removal of the lens is then no longer guaranteed. Thus, several fiber arranged around a suction channel for removed material or a flushing fluid channel are advantageous, as is, under certain circumstances, an adapted emerging direction of the light, brought about through fiber ends with certain cuts. All the aforementioned possibilities are also of great advantage when removing the vitreous body (vitrectomy). In some cases it makes sense for the laser light to emerge laterally (e.g. at 90° to the light within the light-conducting element) so as to avoid direct damage of, for example, the retina during the vitrectomy. Furthermore in trabeculotomy it is possible to create a precise and defined small opening in the eye and to create from the inside a suitable channel for the controlled flowing out of the chamber fluid. Finally, due to the very good adjustment possibilities of the laser described here a precise correction of the lens, hitherto unknown for mid IR lasers, can be carried out, which also brings about the advantage of the sharply reduced acquisition and maintenance costs compared to an excimer laser or a femtosecond laser. Ideally the medical laser device is capable to accept several handpiece units or fiber units with handpieces to cover a broad or even the whole range of eye and eye related surgery and correction treatments (incl. rhexis and many more).

III.)
A medical laser device,
comprising a laser described in this application,
comprising a coupling unit allowing the optimum coupling of the laser light into at least one light-guiding element (e.g. fiber optic, hollow fiber optic, articulated mirror arm),
coupled to at least one light-guiding element, which is designed to be interchangeable and possibly also sterilisable or as a disposable component
(at least one) of these light-guiding elements is connected to a handheld device, which may be interchangeable and possibly also sterilisable or designed as a disposable component
the handheld device possibly a further comprises a coupling unit, which optimally couples the laser light into at least one of the light-guiding elements and then on to the point to be treated or into a light-guiding element, which may be interchangeable and possibly also sterilisable or designed as a disposable component
in addition to at least one of these light-guiding elements possibly also an accompanying tube for fluids and/or gases which are pumped away from the device and/or sucked in and/or electrical leads (e.g. switching contact signals, indication signals . . . ) and/or optical lines for transmitting data from the point to be treated or to conduct light (illumination, laser light, target lasers . . . ) to the point to be treated
for the treatment of diseases of the (animal or human) brain or other organs in order remove tissue parts in a precise and defined manner. An example is treatment of brain centres which, for example, cause epilepsy, whereby precise removal of areas considered to be diseased can take place. Another possibility is the removal of deposits in or on blood vessels (e.g. arteriosclerosis). An example is the increasing calcification of the carotid artery in a very large population group over the age of approximately 50 years. The deposit is usually found within the mantle of the blood vessel but outside the vessel conveying the blood. Here too the laser has to be very finely adjusted, both in terms of the pulse energy and the repetition rate. In both cranial and vascular surgery short pulse durations are necessary to ensure little thermal destruction of the surrounding tissue, but not too short so a not to produce any shock waves which in turn give off mechanical energy into the surrounding tissue thereby destroying it. The optimum pulse is around 1 to 50 us (see also the publication by Joseph T. Walsh, 1981, Pulsed Laser Ablation of Tissue: Analysis of the removal process and tissue healing, this document is incorporated into this application) and is also dependent on the set pulse energy as well as the number of light-conducting elements leading to the site to be treated.

IV.)
A medical laser device,
comprising a laser described in this application,
comprising a coupling unit allowing the optimum coupling of the laser light into at least one light-guiding element (e.g. fiber optic, hollow fiber optic, articulated mirror arm),
coupled to at least one light-guiding element, which is designed to be interchangeable and possibly also sterilisable or as a disposable component
(at least one) of these light-guiding elements is connected to a handheld device, which may be interchangeable and possibly also sterilisable or designed as a disposable component
the handheld device possibly a further comprises a coupling unit, which optimally couples the laser light into at least one of the light-guiding elements and then on to the point to be treated or into a light-guiding element, which may be interchangeable and possibly also sterilisable or designed as a disposable component
in addition to at least one of these light-guiding elements possibly also an accompanying tube for fluids and/or gases which are pumped away from the device and/or sucked in and/or electrical leads (e.g. switching contact signals, indication signals . . . ) and/or optical lines for transmitting data from the point to be treated or to conduct light (illumination, laser light, target lasers . . . ) to the point to be treated.
for the treatment of diseases of (animal or human) bones. Treatment with this laser is predestined for the surgery of fused auditory ossicles (separation from each other or from tissue proliferations, stapetoplastics) as well as operations on bones in the hand and cranio-maxillofacial surgery, where damage to the facial nerve through lack of precise methods must be avoided. A further major advantage of the laser described here is the possibility of bringing about considerably less thermal destruction in the bone tissue than a flash light pumped laser or a mechanical working instrument. The healing process is thereby optimised and many times faster. The bone cells can grow together more easily as coagulation and/or carbonisation hardly occur and the bone cells can therefore connect directly again and the joint is surrounded by considerably less proliferation. In addition to the treatment of bones, the treatment of cartilage and intervertebral disk tissue forms part of orthopaedics. Proliferations in joints can also be smoothed in a precise and defined manner in order to thereby reduce and even eliminate pain. Another area of application is the preparation of bones in the event of fractures in order to temporarily or permanently affix connection elements, such as drilling holes for screws and other implants. In the case of already adhered or incorrectly/poorly knitted fractures a breakage point can be precisely prepared so that the fracture can optimally grow together. Another area of application is the precise removal of cancer cells in bone, such as, for example giant cell tumours or other benign or malignant growths.

In dermatology the laser parameters can be varied in such a way that on the one hand with very short pulses they bring about ablation with very low or negligible thermal input into the surrounding tissue, and on the other hand in the deeper skin layers they produce thermal activation of collagen shrinkage or stimulation of the fibrillae growth by way of long pulses and high repetition rates through heat stacking occurring so that the energy also gives off heat to the tissue surrounding the pore or ablation zone.

For the above forms of embodiment the laser itself or the light-guiding element can be mounted on a positioning device, which is either moved automatically along at least one axis in the X, Y and/or Z direction over a pre-programmed path, or manually in the space. Furthermore, the target can be moved manually or in a pre-programmed manner under the laser in up to all three dimensional axes. A beam deflector can also be fitted directly after the laser or the light-conducting element, which deflects the laser beam in at least one axis in a manual or pre-programmed manner. Precise operation is facilitated by means of operation aids, such as, for example, on-line X-ray monitoring or other processes such as, for example, OCT (optical coherence tomography) with which the treating doctor can see online and accurately where he/she is ablating which material at that time. Differences in tissue (bone and nerve tissue, calcifications in a blood vessel, e.g. arteriosclerosis etc.) can be recognised, and the dimensional extent of material to be ablated or already ablated can be monitored and taken into account.

The laser parameters are controlled via the driver or the "semiconductor laser", the laser diode driver, which controls various operating modes such as continuous wave, quasi continuous wave (pulsed), gain switched. The pulse repetition rate, the pulse energy (via the current of the "semiconductor lasers"), the pulse form (saw-tooth, sinus, rectangular, trapezoidal, . . . ) and the rise and fall times can be controlled. Usually a rectangular pulse with short rise and fall times is selected in order to prevent unnecessary thermal loading in the laser crystal. The longer the supply lines between the laser diode driver and the laser, the slower the rise time and sometimes also the fall times due to lead inductivities and/or resistance through the skin effect, and the more energy is unused or inefficiently pumped to the laser crystal. It is particularly advantageous if the laser diode driver is mounted close to the laser. The most important parameters such as current, repetition rate pulse duration of the laser diode driver can be set by the user, as the almost directly correspond with the generated laser pulses.

Light-guiding elements can be articulated mirror arms, hollow fibers, light-conductors and other single or multiple glass fibers based on sapphire, germanium oxides, silicon oxides or based on fluorides or ceramic fibers that are currently being developed, such as, for example, transparent aluminium, zirconium, magnesium etc, based ceramics which are currently under development.

Method of coupling for light-guiding elements, above all for multiple light-guiding elements are known to a person skilled in the art. However, the cost-effectiveness of these is essential. For reasons of space it is rational to couple multiple light conducting elements in the base station. As in the mid-infrared range the light conducting elements are very expensive, coupling tends to be carried out in a handheld device with just one fiber leading to the handheld device where it is split into several light-conducting elements and taken to the tip of the handheld device.

| | Reference number list |
|---|---|
| 1 | Solid-state laser |
| 2 | Laser gain medium |
| 3 | Resonator structure |
| 4 | End faces |
| 5 | Pump source |
| 6 | Conductive cooler |
| 7 | reflector |
| 8 | |
| 9 | |
| 10 | |
| 11 | |
| 12 | |
| 13 | |
| 14 | |
| 15 | |
| 16 | |
| 17 | |
| 18 | |
| 19 | |
| 20 | Handheld device |
| 21 | Laser beam |
| 22 | Optical pathway |
| 23 | Target surface |
| 24 | Beam formation, deflection unit |
| 25 | Contact window |
| 26 | Laser beam |
| 27 | Covering |
| 28 | Mirror |
| 29 | Cooling unit |
| 30 | cavity |
| 31 | Tube |
| 32 | Control unit |
| 33 | Current buffer |
| 34 | Supply line |
| 35 | Control switch unit |
| 36 | Connector |
| 37 | Flexible hose |
| 38 | Connector means |
| 39 | Standalone handheld device |
| 40 | Phase state change material |
| 41 | Electrical energy storage means |
| 42 | Connection port |
| 43 | User interface |
| 44 | Housing |
| 45 | Light guiding element |
| 46 | Optical coupling device |
| 47 | Device for generating pressurized gas |
| 48 | Waste compartment |
| 49 | Flexible hose |
| 50 | Handheld unit, handheld device |
| 51 | Duct |
| 52 | Working end, working tip |
| 53 | Outlet port |
| 54 | Working cap, protective cap |
| 55 | Operation switch |
| 56 | Control unit |
| 57 | Connector means |
| 58 | Duct |
| 59 | Working tip end |
| 60 | Duct |
| 61 | Fiber |
| 62 | Outlet port for pressurized liquid |
| 63 | Outlet port for pressurized gas |
| 64 | Illumination means |
| 65 | Image gathering means |
| 66 | Skew surface |

The invention claimed is:

1. A monolithic, side pumped solid-state laser comprising a laser resonator structure comprised of a laser gain medium having a longitudinal axis, wherein the laser resonator structure comprises end faces forming a linear optical path resonant cavity there between, the end faces comprising at least partially reflecting laser mirrors, one high reflector and an output coupler, deposited on the end faces, the laser gain medium comprising a side face for receiving pump light generated by a diode laser of a pump source, and comprising a conductive cooler, and comprising a reflector arranged opposite to the side face with respect to the longitudinal axis, wherein the laser gain medium is a low gain material, wherein the low gain material is a laser gain media with a stimulated emission cross section equal or less than that of Er:YAG namely $<=3.0*10^{-20}$ cm$^2$, wherein the conductive cooler comprises contact faces for contacting the laser gain medium, and wherein due to the monolithic design of the lasers, a laser high reflector is deposited directly on the gain medium and an output coupler is deposited directly on the opposite end on the gain medium.

2. The solid-state laser according to claim 1, wherein the laser gain medium has a cross sectional area of less than 7.5 mm$^2$.

3. The solid-state laser according to claim 2, wherein the contact faces are symmetrically arranged with respect to the longitudinal axis of the laser gain medium.

4. The solid-state laser according to claim 3, wherein the conductive cooler comprises a cooler cavity arranged beside the laser gain medium and arranged opposite to the side face, and wherein the pump light reflector is arranged in the cooler cavity.

5. The solid-state laser according to claim 4, wherein the diode laser and the reflector are arranged in such a way with respect to the longitudinal axis that there is equal distance between the longitudinal axis and each of the diode laser and the longitudinal axis and the reflector, so that the length of the optical path between the pump source and the longitudinal axis is the same as the length of the optical path between the longitudinal axis and the reflector.

6. The solid-state laser according to claim 2, wherein both end faces comprise a laser mirror, wherein one of the laser mirrors is a high reflecting laser mirror, in particular having a reflectivity of 99% to 100%, and wherein the other laser mirror is an output coupler.

7. The solid-state laser according to claim 2, wherein the laser resonator structure emits a wavelength in the range of 1700 nm to 3200 nm.

8. The solid-state laser according to claim 7, wherein the output coupler has a reflectivity in the range of between 92.5% and 99%.

9. The solid-state laser according to claim 1, wherein the laser gain medium has free ends which are not arranged within the cooler.

10. The solid-state laser according to claim 1, wherein the laser gain medium comprises a rare-earth-doped YAG or YSGG or YLF crystal host, with neodymium, ytterbium, erbium, thulium, chromium and/or holmium doping.

11. The solid-state laser according to claim 1, wherein the wavelength of the diode laser is selected such that the main wavelength of the diode laser is shifted relative to an absorption peak region of the laser gain medium.

12. The solid-state laser according to claim 11, wherein the wavelength of the pump light is selected at a low absorption coefficient of the laser gain medium.

13. The solid-state laser according to claim 1, wherein the conductive cooler comprises contact faces contacting the laser gain medium and also holds the laser gain medium, the conductive cooler consisting of metal, ceramics or a crystal-line material.

14. The solid-state laser according to claim 13, comprising two contact faces, wherein the contact faces are symmetrically arranged with respect to the longitudinal axis of the laser gain medium, opposite to each other.

15. The solid-state laser according to claim 1, wherein the conductive cooler comprises an outer tubular member concentrically arranged with respect to the longitudinal axis, the outer surface of the laser gain medium and the outer tubular member defining an internal space for a cooling fluid.

16. The solid-state laser according to claim 1, comprising at least two pump sources spaced apart in circumferential direction with respect to the longitudinal axis, and further comprising a corresponding pump light reflector arranged opposite to the side face with respect to the longitudinal axis.

17. The solid-state laser according to claim 1, comprising a lens and comprising an optical fiber having a diameter between 100 μm and 250 μm, wherein the lens is arranged to focus a laser beam of the solid-state laser into the optical fiber.

18. The solid-state laser according to claim 1, wherein the laser gain medium is of cylindrical shape or elliptical-cylindrical shape.

19. The solid-state laser according to claim 1, wherein at least the partially reflecting laser mirror is deposited on the end face of the laser gain medium, and wherein the layer deposited thereon has a packing density of greater than 0.9.

20. The solid-state laser according to claim 1, wherein the pump source has a wavelength between 955 to 985 nm.

21. The solid-state laser according to one of claim 1, wherein the pump source has a wavelength between 760 to 815 nm.

22. The solid-state laser according to claim 1, wherein the pump source has a wavelength between 1600 to 2050 nm.

23. The solid-state laser according to claim 1, wherein the pump light is fed through a side face into the laser gain medium, wherein from 30 to 70% of the pump light is exiting the laser gain medium at an opposite side face as an exiting pump light, and wherein the exiting pump light is reflected by the reflector, such that a reflected pump light is reentering the laser gain medium at the opposite side face.

24. The solid-state laser according to claim 1, wherein the pump source is embodied as a laser-diode array, arranged parallel the longitudinal axis.

25. A method for operating a monolithic, side pumped solid-state laser according to claim 1, comprising a laser resonator structure comprised of a laser gain medium having a longitudinal axis, wherein pump light is fed through a side face into the laser gain medium, wherein a part of the pump light is exiting the laser gain medium at an opposite side face as an exiting pump light, and wherein the exiting pump light is reflected on a reflector as reflected pump light, such that a reflected pump light is reentering the laser gain medium at the opposite side face.

26. A method for operating the solid-state laser according to claim 25, wherein the laser gain medium is cooled symmetrically with respect to the longitudinal axis of the laser gain medium, so as to receive in the laser gain medium with respect to the longitudinal axis a symmetrical thermal distribution.

27. A method for operating the solid-state laser according to claim 25, wherein the main wavelength of the pump light is shifted relative to an absorption peak region of the laser gain medium.

28. Treatment device comprising a solid-state laser, arranged in a housing and emitting a laser beam, an optical coupling device, directing the incident laser-beam into a light guiding element, a flexible hose, connecting the solid-state laser with a handheld device and comprising the light guiding element, wherein the handheld device comprises an outlet port for the distal end of the light guiding element, for directing the laser-beam to a target surface, wherein the solid-state laser is embodied according to claim 1.

29. The treatment device according to claim 28, wherein the housing comprises a power supply with a high current capacity buffer.

30. The treatment device according to claim 28, wherein the housing comprises a device for generating a pressurized gas, in particular with a positive and/or negative relative pressure.

31. The treatment device according to claim 28, wherein the housing comprises a device for generating a pressurized liquid.

32. The treatment device according to claim 28, wherein the flexible hose comprises at least one duct, for transporting a liquid or a gaseous medium to and/or from the handheld device.

33. The treatment device according to claim 28, wherein the housing comprises a detachable connector.

34. The treatment device according to claim 28, wherein the handheld device comprises a detachable connector.

35. The treatment device according to claim 28, wherein the handheld device comprises a beam formation and/or deflection unit.

36. The treatment device according to claim 28, wherein the handheld device comprises a sound transducer, in particular an ultrasonic sound transducer.

37. The treatment device according to claim 28, wherein the handheld device comprises a light guiding element, and wherein the light guiding element comprises a beam splitting unit.

38. The treatment device according to claim 28, wherein the handheld device comprises an optical imaging device.

39. The treatment device according to claim 28, wherein the handheld device comprises a radio-frequency transmitter.

40. The treatment device according to claim 28, wherein the flexible hose comprises a power supply cable.

41. The treatment device according to claim 28, wherein the flexible hose comprises at least one data transmission line.

42. The treatment device according to claim 28, wherein the light guiding element is embodied as a single fiber light guiding element.

43. The treatment device according to claim 28, wherein the light guiding element is embodied as a multi fiber light guiding element.

44. The treatment device according to claim 28, wherein the outlet port comprises an outlet opening.

45. The treatment device according to claim 44, wherein the outlet opening is arranged at least partly around the distal end of the light guiding element.

46. The treatment device according to claim 28, wherein the light guiding element ending is arranged at least partly around the outlet opening.

47. Treatment device comprising a handheld device, a table-top unit, and a flexible hose,
   wherein the handheld device comprises:
      a solid-state laser emitting a laser beam,
      a laser beam formation and deflection unit, and
      a contact window,
   wherein the solid-state laser comprises
      a cooling unit, and
      a control unit electrically driving the pump source of the solid-state laser,
   wherein the contact window emits the formed laser beam from the handheld device to a target surface and comprises a transparent covering,
   wherein the solid-state laser, the beam formation and deflection unit, and the contact window form an optical pathway,
   wherein the table-top unit comprises an electrical power supply and comprises a cooling liquid circulation system,
   wherein the flexible hose connects the table-top unit with the handheld device and comprises an electrical power supply connection,
   wherein the solid-state laser is embodied according to claim 1,
   wherein the cooling unit comprises a cooling cavity,
   wherein the flexible hose further comprises at least two cooling liquid transportation tubes connecting the cooling cavity with the cooling liquid circulation system of the table-top unit, and
   wherein the control unit comprises one high current capacity buffer.

48. Treatment device according to claim 47, wherein the optical pathway is sealed against the surrounding environment, using sealing elements and/or smooth planes fitting each other.

49. Treatment device according to claim 47, wherein the handheld device, comprises at least two high current capacity buffers and a switching unit, for individually connecting one of the high current capacity buffers to the control unit.

50. Treatment device according to claim 47, wherein the handheld device comprises a user interface, comprising a display unit, and an input device.

51. Treatment device according to claim 47, wherein the handheld device comprises an image acquisition unit and an image analysis unit.

52. Treatment device according to claim 47, wherein the handheld device is detachable from the table-top unit.

53. Treatment device according to claim 47, wherein the transparent covering is detachable from the handheld device.

54. Treatment device comprising a handheld device comprising:
   a solid-state laser emitting a laser beam,
   an electrical energy storage unit,
   a laser beam formation and deflection unit, and
   a contact window,
   wherein the laser comprises:
      a cooling unit, and
      a control unit electrically driving the solid-state laser,
   wherein the contact window emits the formed laser beam from the handheld device to a target surface and comprises a transparent covering,
   wherein the solid-state laser, the beam formation and deflection unit, and the contact window form an optical pathway,
   wherein the solid-state laser is embodied according to claim 1,
   wherein the cooling unit is embodied as a solid-state cooling device, and
   wherein the control unit comprises one high current capacity buffer.

55. Treatment device according to claim 54, wherein the solid-state cooling device is a phase change material.

* * * * *